United States Patent [19]
Tsuji et al.

[11] Patent Number: 5,543,831
[45] Date of Patent: Aug. 6, 1996

[54] ENDOSCOPE SYSTEM HAVING REDUCED NOISE EMISSION/PERMEATION

[75] Inventors: Kiyoshi Tsuji, Musashino; Akinobu Uchikubo, Hachioji; Kenji Kimura, Tachikawa; Masahito Goto, Hachioji; Tsutomu Hirai, Sagamihara, all of Japan

[73] Assignee: Olympus Optical Co., Ltd., Tokyo, Japan

[21] Appl. No.: 26,203

[22] Filed: Mar. 2, 1993

Related U.S. Application Data

[63] Continuation of Ser. No. 642,749, Jan. 18, 1991, abandoned.

[30] Foreign Application Priority Data

Nov. 20, 1990 [JP] Japan .................................. 2-315106

[51] Int. Cl.⁶ ............................... H04N 7/18; A61B 1/00
[52] U.S. Cl. ............................... 348/65; 348/75; 128/901; 128/908
[58] Field of Search ............................ 358/98, 160, 167; 128/6, 901, 908; 348/65, 75, 76

[56] References Cited

U.S. PATENT DOCUMENTS

| | | | |
|---|---|---|---|
| 4,615,330 | 10/1986 | Nagasaki et al. | 348/65 |
| 4,816,909 | 3/1989 | Kimura et al. | 358/98 |
| 4,853,772 | 8/1989 | Kikuchi | 358/98 |
| 4,868,647 | 9/1989 | Vehara et al. | 358/98 |
| 4,888,639 | 12/1989 | Yabe et al. | 358/98 |
| 4,901,142 | 2/1990 | Ukuno et al. | 358/98 |
| 4,931,867 | 6/1990 | Kikuchi | 358/98 |
| 4,974,075 | 11/1990 | Nakajima | 348/65 |
| 5,038,780 | 8/1991 | Boetzkes | 128/901 |
| 5,134,547 | 7/1992 | Takamizawa | 348/65 |
| 5,174,293 | 12/1992 | Hagiwara | 348/65 |
| 5,309,918 | 5/1994 | Schraag | 128/908 |

OTHER PUBLICATIONS

Newark Electronics Catalog No. 109, Jan. 1988, pp.294–295.

*Primary Examiner*—Thai Q. Tran
*Assistant Examiner*—Bryan S. Tung
*Attorney, Agent, or Firm*—Armstrong, Westerman, Hattori, McLeland & Naughton

[57] ABSTRACT

A medical system having an endoscope probe intubated into a body, a signal processing circuit for processing a signal for the probe and an electric source circuit insulated from a commercial electric source. A part of the signal processing circuit connected to the probe is isolated by an isolation circuit to secure the safety. An impedance element is employed to prevent a malfunction by reducing an emission/permeation of noises. No adverse influence is thereby exerted on outside units.

5 Claims, 21 Drawing Sheets

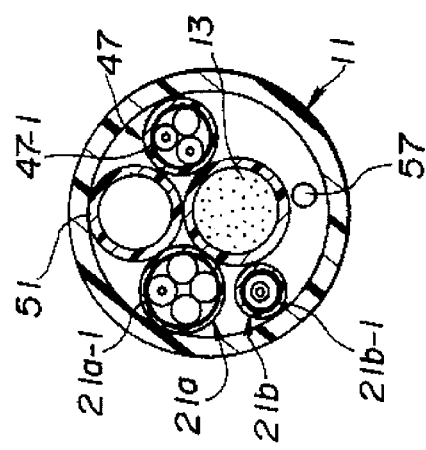
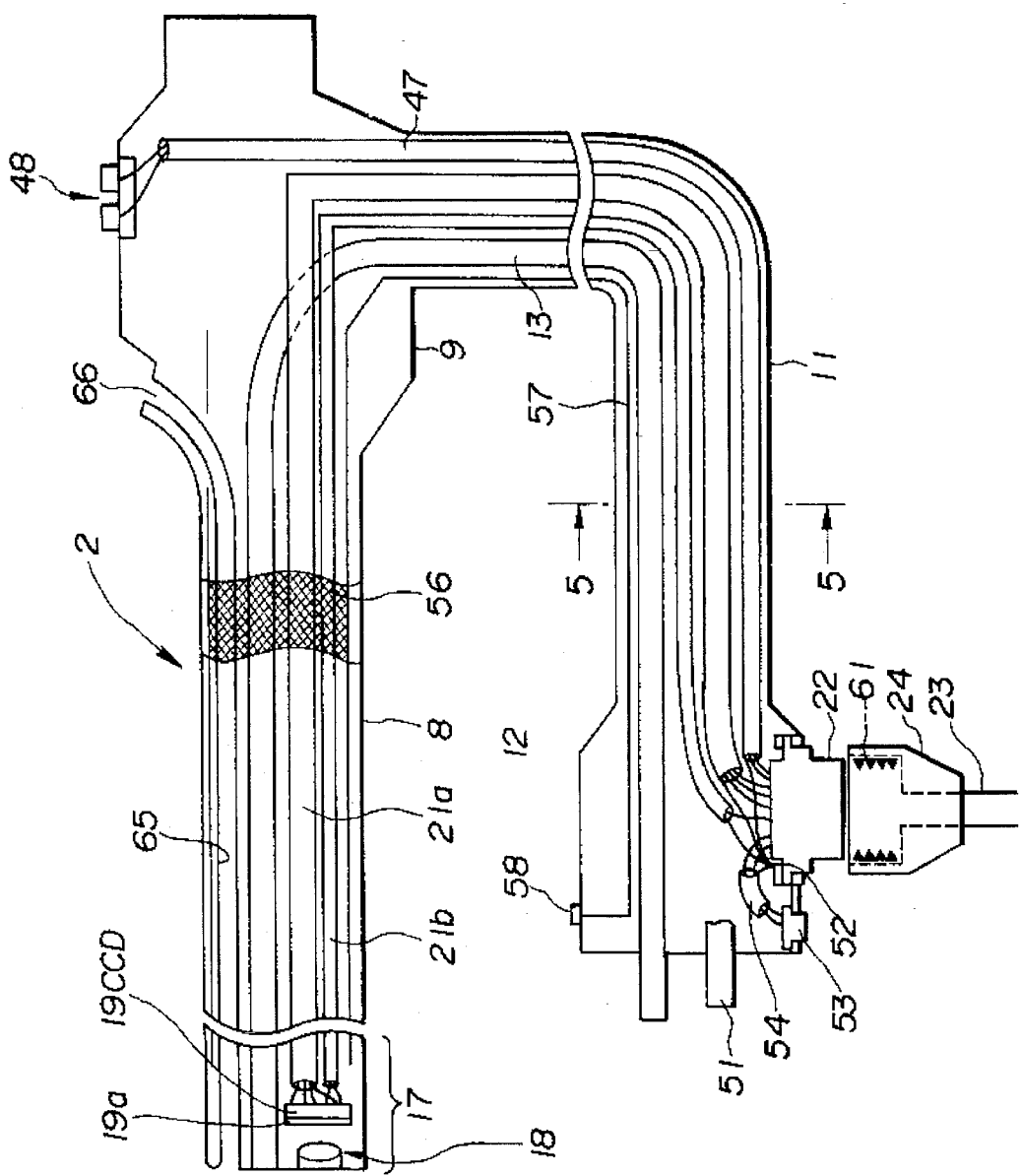

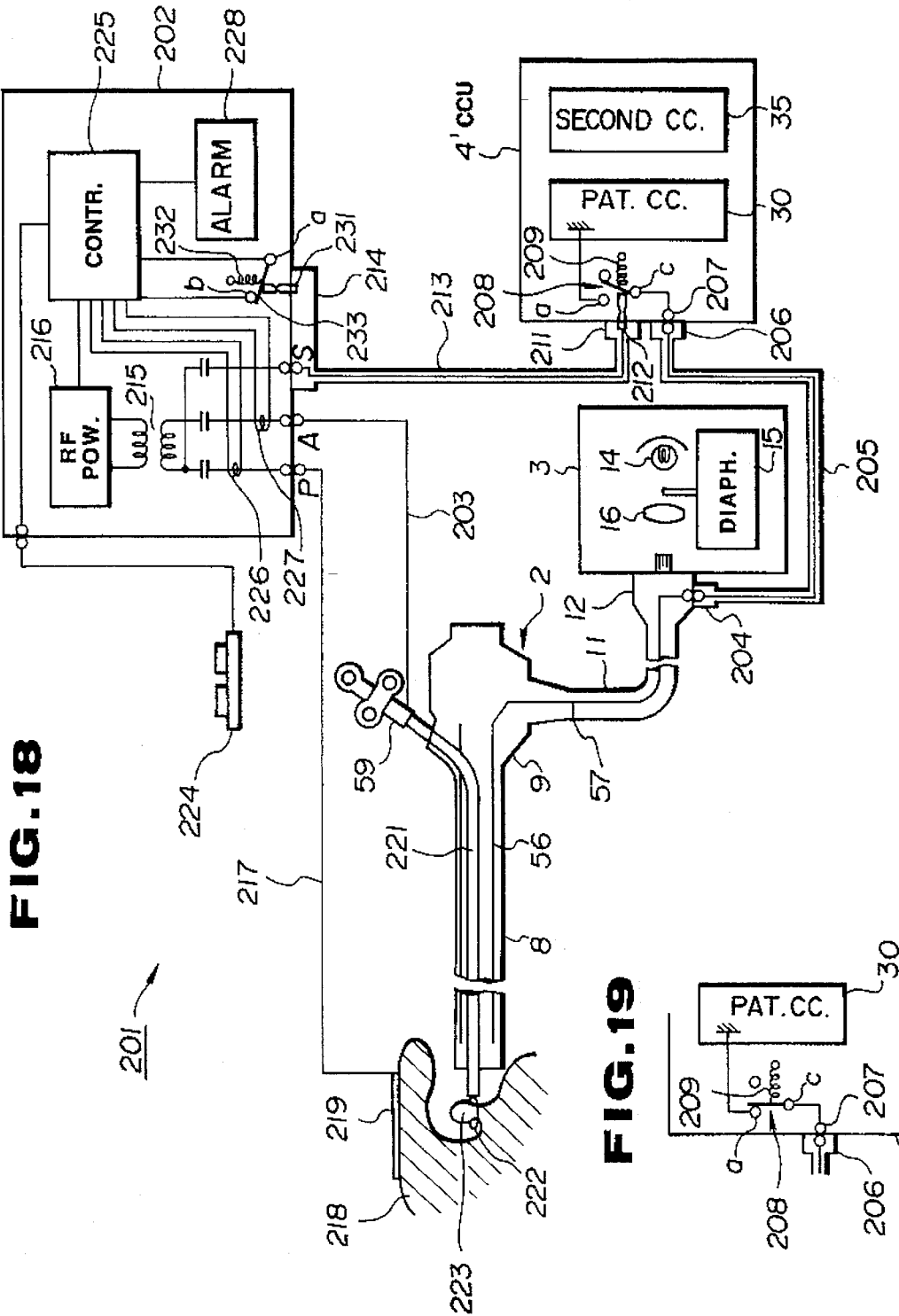

5,543,831

ENDOSCOPE SYSTEM HAVING REDUCED NOISE EMISSION/PERMEATION

This application is a continuation of application Ser. No. 07/642,749, filed Jan. 18, 1991, now abandoned.

BACKGROUND OF THE INVENTION

Field of the Invention and Related Art Statement

The present invention relates to a medical system having a means for reducing an emission and permeation of undesirable noises.

In recent years, an endoscope has widely been utilized. The endoscope is capable of observing an organ within a body cavity by intubating an elongate intubation unit into the body cavity. The endoscope is also capable of performing a variety of cure treatments by use of a treatment tool inserted in a treatment tool channel as the necessity arises.

In addition, a variety of electronic endoscopes have hitherto been proposed. In those endoscopes, a tip of the intubation unit is provided with a solid-state imaging element such as a charge coupled device (CCD) as an imaging means. The image information is fetched as a photoelectrically-converted electric signal.

In the case of the electronic endoscope system conceived as a medical system, a circuit unit (patient circuit) intubated into a patient body and a circuit unit (secondary circuit) connected to peripheral units such as a monitor or the like are, as disclosed in, e.g., U.S. Pat. No.4,931,867, isolated by an isolation means to ensure safety.

Namely, if no isolation is effected by the isolation means, and when the isolation from the ground (abbreviated as GND) is declined or deteriorated due to an accident, an electric current is expected to flow down to GND via a human body into which the endoscope intubated. Presumably, this creates a highly dangerous situation. In contrast, however, the patient circuit is isolated from the secondary circuit by the isolation means. In this case, even if the decline of isolation happens, the current flows to GND on the side of only one circuit, thereby ensuring the safety. For instance, when running in the patient circuit alone, the current is low, and hence the patient is only slightly influenced. When running in only the secondary circuit, the patient is protected because of the patient circuit being insulated.

GNDs of the patient circuit and the secondary circuit are not, however, made common by the isolation means. This in turn makes easy a radiation of signals as electric waves outside the system via a floating capacity or the like. Besides, the electric waves from the outside readily intermix (permeate) in an interior of the system via the floating capacity.

For example, the electric signals employed in the electronic endoscope system are radiated to other electric devices. This results in a possibility to produce noises (referred to as radiant noises) which cause a malfunction. Moreover, noises (referred to as radiant noises) radiated from other electronic devices tend to intermix in the electronic endoscope system. For instance, video signals are intermixed with the noises, with the result that a quality of the endoscope image declines. When control signals are intermixed with the noises, this causes a malfunction.

In general, a variety of signals assuming different levels are dealt with inside the electronic endoscope system, For this reason, it is desirable to have a function to restrain the unnecessary radiation of noises as much as possible and also the permeation of the radiated noises.

In a recent situation, it is increasingly desirable to take sufficient countermeasures against EMC (a generic name of EMI (a problem of causing an electromagnetic interference) and EMS (a problem of undergoing the electromagnetic interference)) typically with respect to the electric equipment.

SUMMARY OF THE INVENTION

It is a primary object of the present invention to provide a medical system such as an electronic endoscope system capable of sufficiently restraining and reducing a radiation and permeation of undesirable noises.

It is another object of the present invention to provide a medical system capable of minimizing malfunctions and exhibiting high safety.

To accomplish the objects described above, according to one aspect of the invention, there is provided a medical system comprising: an electronic endoscope probe intubatable in a body cavity or the like; a patient circuit, to which the probe is detachably connected via a connector, for processing a signal for the probe; and a signal processing means having a secondary circuit isolated from the patient circuit by an isolation means. In this medical system, at least one of the patient circuit, the probe and the secondary circuit includes a noise reducing means for reducing a radiation or a permeation of noises. With this arrangement, the noises radiated from the medical system towards the outside can be reduced, or the noises which permeate from the outside can be reduced.

BRIEF DESCRIPTION OF THE DRAWINGS

Other objects and advantages of the present invention will become apparent during the following discussion taken in conjunction with the accompanying drawings, in which:

FIGS. 1 through 15 show one embodiment of this invention;

FIG. 1 is a block diagram illustrating a whole construction of a camera control unit;

FIG. 2 is a block diagram depicting a construction of a signal processing system of the camera control unit;

FIG. 4 is a block diagram illustrating an electronic scope;

FIG. 5 is a sectional view taken substantially along the line 5—5 of FIG. 4;

FIG. 6 is a sectional view schematically illustrating a structure of a cable connector;

FIG. 7 is an enlarged explanatory diagram showing a part of the cable connector of FIG. 6;

FIG. 8 is a perspective view schematically depicting a connector receiver incorporated in the camera control unit;

FIG. 9 is a perspective view illustrating the rear side of FIG. 8;

FIG. 10 is an explanatory diagram showing a part of the construction of FIG. 1;

FIG. 11 is an explanatory diagram showing an arrangement that a patient circuit is connected via a capacitor to both of GNDs of a secondary circuit;

FIG. 12 is a perspective view depicting a shield case;

FIG. 13 is an enlarged side elevation showing a part of the shield case of FIG. 12;

FIG. 14 is an explanatory diagram showing weep holes;

FIG. 15 is a plan view showing the periphery of a primary circuit;

FIGS. 18 and 19 in combination show a second embodiment of the present invention;

FIG. 18 is a block diagram illustrating the principal portion of the second embodiment;

FIG. 19 is an explanatory diagram illustrating the principal portion of the camera control unit in a state where no connector is connected;

FIG. 21 is a block diagram depicting a surgical operation system in the fourth embodiment;

FIG. 22 is a block diagram illustrating a configuration of the control unit;

FIG. 23 is a sketch drawing depicting an ultrasonic endoscope in the fifth embodiment;

FIG. 24 is a block diagram showing a variant form of the fifth embodiment of this invention;

FIG. 26 is a sketch drawing depicting a burning anastaltic device in the sixth embodiment;

FIG. 27 is a block diagram schematically illustrating a signal processing system;

FIG. 28 is a sketch drawing depicting an electrohydraulic lithotriptor in the seventh embodiment;

FIG. 29 is a perspective view illustrating a tip of a discharge probe; and

FIG. 30 is a block diagram schematically illustrating the signal processing system of a discharge control unit.

DETAILED DESCRIPTION OF THE PREFERRED EMBODIMENTS

Figure 1:
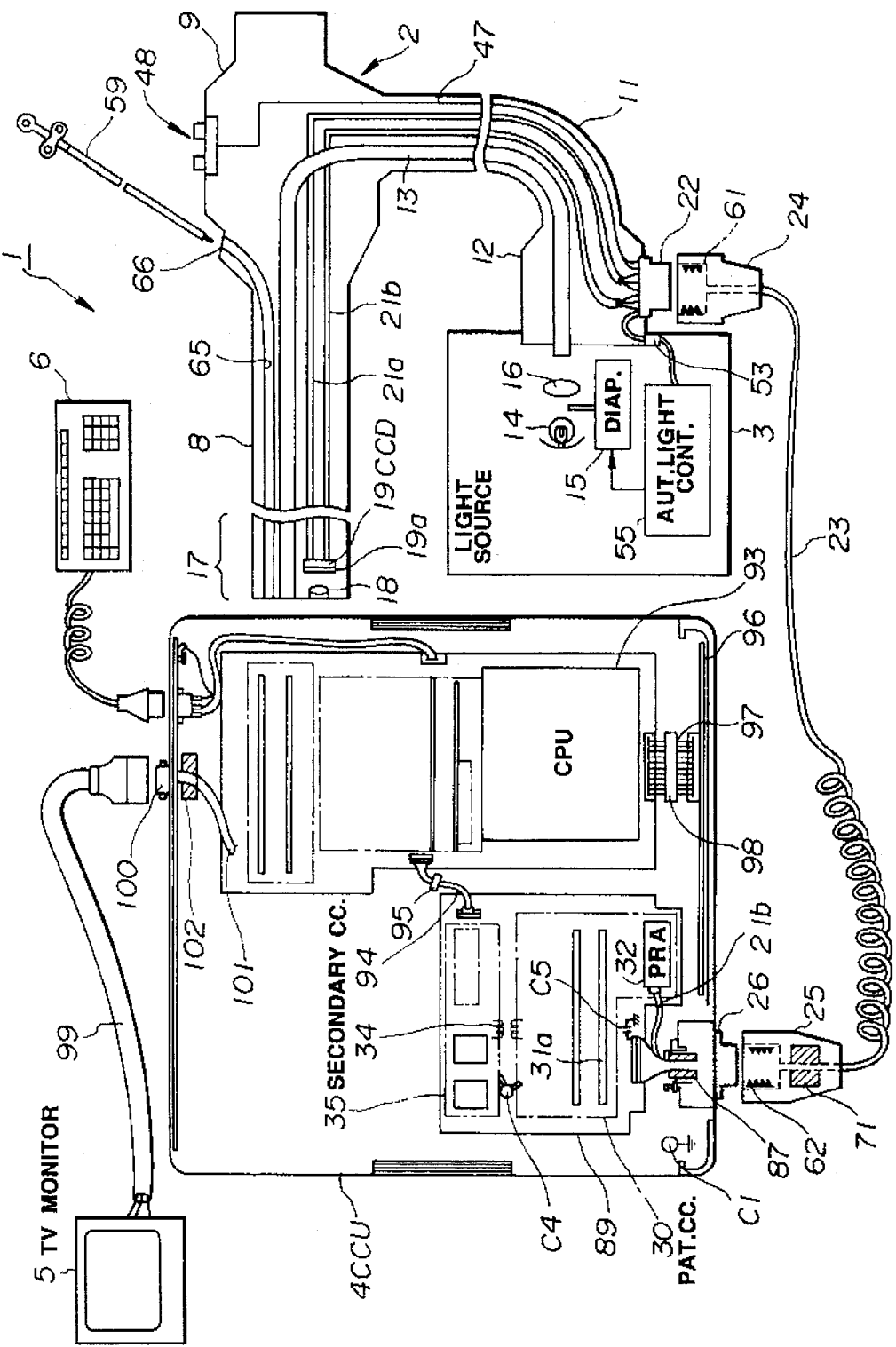

Referring to FIG. 1, an electronic endoscope system 1 in a first embodiment comprises an electronic scope 2, a light source 3, a video processor or camera control unit (hereinafter abbreviated to CCU) 4, a TV monitor 5 and a keyboard 6. The electronic scope 2 incorporates an imaging means. The light source 3 supplies illumination light to the scope 2. The CCU 4 processes signals with respect to the electronic scope 2. The TV monitor 5 displays standard video signals processed by the CCU 4. The keyboard 6 connected to the CCU 4 serves to input the data such as comments associated with endoscope images displayed on the TV monitor 5.

As depicted in FIG. 1 or 4, the electronic scope 2 includes an elongate intubation unit 8 exhibiting a flexibility enough to be intubated into a body cavity. A manipulation unit 9 having a large width is formed at the rear end (proximal end) of the intubation unit 8. A universal cable 11 extends outwards from the manipulation unit 9. Secured to the terminal of the universal cable 11 is a light source connector 12 detachably attached to the light source 3.

A light guide 13 for transmitting the illumination light is inserted through the universal cable 11 as well as through the intubation unit 8. The connector 12 is attached to the light source 3, whereby the illumination light from a lamp 14 provided in the light source 3 travels through a diaphragm 15. The illumination light is condensed by a lens 16. An end surface of the light guide 13 is irradiated with the condensed light. The illumination light transmitted via the light guide 13 is emitted forwards from the other end surface fitted to the tip 17 of the intubation unit 8. A subject, i.e., the affected part, is illuminated with the light emitted therefrom. An image of the illuminated subject is formed on an imaging surface of the CCD 19 defined as a solid-state imaging device disposed on a focal plane of an objective lens 18 provided at the tip 17 by use of this objective lens 18. Fitted to the imaging surface of the CCD 19 is a mosaic filter 19a for optically separating the colors, for instance, per pixel. Furthermore, the CCD 19 effects a photoelectric conversion into electric signals. The electric signals are accumulated as an electric charge. The CCD 19 is connected to one ends of a driving signal transmission line 21a and a CCD output signal transmission line 21b which are inserted through the universal cable 11 and the intubation unit 8 as well. The other ends of these transmission lines 21a and 21b are led to a connector receiver 22 provided on the side portion of the light source connector 12. Connected detachably to this connector receiver 22 is a connector 24 attached to one end of a signal cable (also referred to as an EL cable) 28. A connector 25 attached to the other end thereof is detachably attached to a signal connector receiver (also referred to as a scope connector receiver) of the CCU 4.

Figure 2:
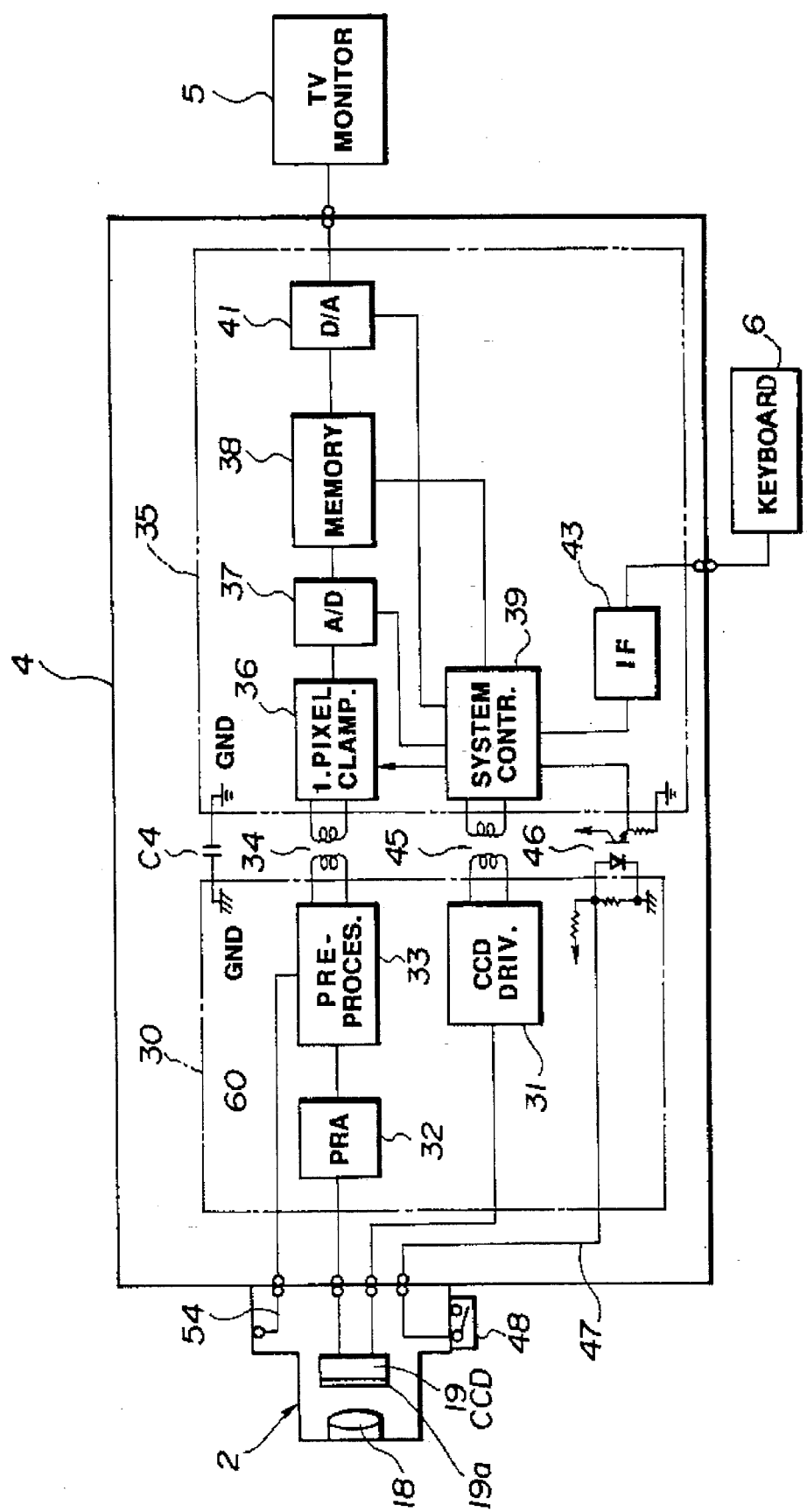

When the two connectors 24 and 25 are connected respectively, as illustrated in FIG. 2, the CCD 19 is supplied with CCD driving signals from a CCD driver 31 constituting a patient circuit 30 in the CCU 4. As a result, the signal electric charges accumulated in the CCD 19 are read out. The readout CCD output signals are amplified by a preamplifier 32 in the CCU 4. Thereafter, the CCD output signals are inputted to a preprocessing circuit 33, whereby these signals are separated into luminance signals and chrominance signals. Additionally, the CCD output signals undergo preprocessing such as a correction or white balance and so on. Subsequent to these preprocesses, the signals are inputted to one-pixel clamp circuit 36 constituting a secondary circuit 35 after passing through an insulation transformer 34. Inputted to this one-pixel clamp circuit 36 are signals DC components of which are eliminated by the insulation transformer 34. Hence, the one-pixel clamp circuit 36 generates the DC components. The DC components are in turn inputted to an A/D converter 37 after passing through an unillustrated low-pass filter, thereby converting into digital signals. Thereafter, the digital signals are stored in a memory 38.

The digital signals stored in the memory 38 are read at a predetermined timing under control of a system controller 39. The digital signals are converted into analog signals by means of a D/A converter 41. Subsequently, the analog signals are outputted together with unillustrated synchronous signals to the TV monitor 5.

The above-mentioned system controller 39 (simply referred to as a controller) is connected via an interface 43 to the keyboard 6. The comments relative to the endoscope images, which are to be displayed on the TV monitor 5, are inputted and may be displayed on a monitor screen.

The controller 39 is connected via the isolation transformer 45 to the CCD driver 31. The CCD driver 31 outputs the readout driving signals to the CCD 19 in response to timing signals transmitted from the controller 39. The controller 39 is connected to a manipulation switch 48 mounted in the manipulation unit 9 of the electronic scope 2 through an isolation circuit 46 employing, e.g., a photocoupler and a control signal line 47 as well. For example, the manipulation switch 48 is composed of a freeze switch for indicating a display of a static picture. When operating the freeze switch, a freeze indication signal is transmitted to the controller 39. The controller 39, when detecting this signal, outputs a write inhibition signal to the memory 38. An update of the data in the memory 38 is inhibited. Therefore, it follows that signals stored in the memory 38 before the write inhibition signal are repeatedly read out. The static image is thereby displayed on the TV monitor 5.

Note that the controller 39 generates and controls a variety of timing pulses. More specifically, the controller 39 controls the clamping operation of the one-pixel clamp circuit 36, A/D converting clocks of the A/D converter 37, read/write of the memory 38 and also D/A converting clocks of the D/A converter 41.

Figure 3A:
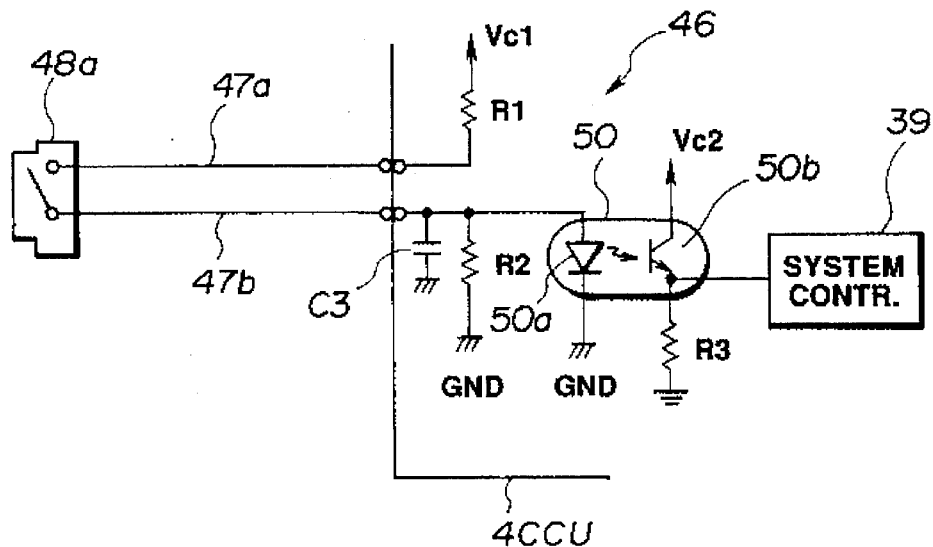
FIGS. 3a and 3b are a circuit diagram showing an isolation circuit.

FIG. 2 or FIG. 3a illustrates the isolation circuit 46 connected to the freeze switch 48a of the manipulation switch 48. A line 47a connected to the switch 48 is connected via a resistance R1 to an electric source terminal Vc1. Another line 47b is connected via a resistance R2 to GND. The line 47b is also connected to an anode of an LED 50 of a photocoupler 50. A cathode thereof is connected to GND of the patient circuit 30. A collector of a photo transistor 50b is connected to an electric source terminal Vc2. An emitter thereof is connected via a resistance R3 to GND of the secondary circuit 35. The emitter is also connected to the controller 39.

The resistance R2 has its resistance value set larger than, e.g., that of the resistance R1. Even when the switch 48a is turned OFF, the lines 47a and 47b are fixed to a constant potential. Radiation and intermixing of noises are thus prevented. Namely, no resistance R2 is provided in the prior art. Hence, during the OFF-state, the potential of the line 47b in the prior art is not established but in a floating state. The prior art has functions associated with a noise generation and a receiving antenna. In this embodiment, however, the line 47b is connected via the resistance R2 to GND. During the OFF-state, the line 47b is kept at the potential of GND, thereby preventing the noise generation and receiving.

When turning ON the switch 48a, a light emitting current is supplied via the resistance R1 to the LED 50a. The LED 50a is thereby lit up. In this case, the lines 47a and 47b are held at a potential approximate to that of the electric source terminal Vc1 or GND.

Figure 3B:
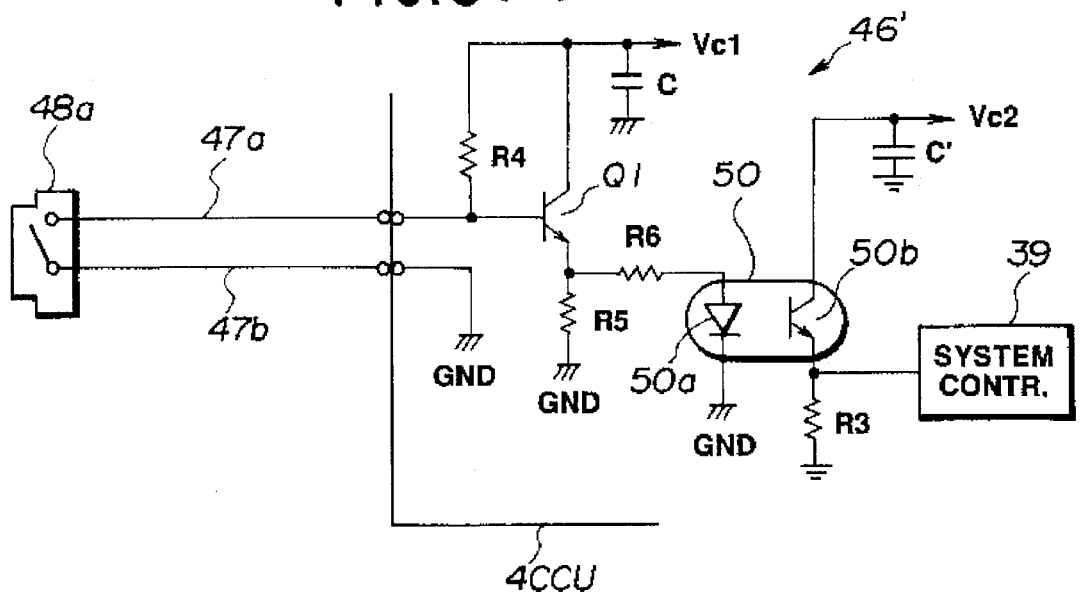

Instead of the isolation circuit depicted in FIG. 3a, an isolation circuit 46' shown in FIG. 3b is also usable.

The circuit 46' is constructed as follows. The line 47a is connected to one end of the switch 48a. The line 47a is also connected via a resistance R4 to the electric source terminal Vc1. The line 47a is further connected to a base of a transistor Q1. Another line 47b is connected to GND of the patient circuit 30.

A collector of the transistor Q1 is connected to the electric source Vc1. An emitter thereof is connected via a resistance R5 to GND of the patient circuit 30. The emitter is also connected via a resistance R6 to the LED 46a.

Other configurations are the same as those of FIG. 3a. Note that the electric source terminal Vc1 of the patient circuit 30 is connected via a capacitor C having a large capacity to GND of the patient circuit 30. The electric source terminal Vc2 of the secondary circuit 35 is connected through a capacitor C' having a large capacity to GND of the secondary circuit 35. (Illustration is omitted in FIG.3a.)

Referring to FIG. 3b, when turning OFF the switch 48a, the potential of the line 47a is similarly fixed to the level of the electric source terminal Vc1 due to the resistance R4. Whereas in the ON-state, the line 47a is fixed to the potential of GND. The same functions as those of FIG. 3a are exhibited.

As illustrated in FIG. 4, the electronic scope 2 is inserted through a driving signal transmission line 21a CCD output signal transmission line 21b and a control signal transmission line 47. Provided is a shield means for shielding the lines 21a, 21b and 47 with shield cover wires 21a-1, 21b-1 and 47-1, separately (synthesis). The respective shield cover wires 21-a, 21b-1 and 47-1 accommodate insulation cover signal lines (including single and coaxial lines). The shield cover wires 21a-1, 21b-1 and 47-1 are covered with insulating sheaths. Note that the numeral 51 in FIG. 5 designates a suction tube. The suction tube is connectable to an unillustrated suction means within the light source 3 by connecting a connector 12 to the light source 3.

The individual transmission lines 21a, 21b and 47 are separately shielded, thereby preventing intermixing of noises between the transmission lines. For instance, the driving signal transmission line 21a supplies the CCD 19 with horizontal transfer driving pulses having a high frequency. The pulses having the high frequency are therefore easy to cause radiant noises. If the noises leak out and permeate in, e.g., the CCD output signal transmission line 21b, the CCD output signals typically assume a feeble level, and hence an S/N ratio largely declines due to an even slight leakage thereof. Contrastingly, shielding is effected by the shield means, thereby preventing the decline of the S/N ratio. As a result, a clear-cut endoscope image can be obtained. If the radiant noises are leaked into the control signal transmission line 47, there arises a possibility in which miscontrol will take place. The miscontrol can be also prevented. It is therefore possible to attain an electronic endoscope system with high safety.

The transmission lines 21a, 21b and 47 are inserted through the universal cable 11 of the electronic scope 2. These lines are connected respectively to unillustrated pins of the connector receiver 22 attached to the side portion of the connector 12. The shield cover wires 21a-1, 21b-1 and 47-1 are one-point-connected to a lug fixed with a screw for fastening a metal sheath frame of the connecter receiver 22.

As depicted in FIG. 4, the connector 12 is provided with a connector member 53 connected to a signal connector receiver of the light source 3. The connector member 53 and the connector receiver 22 are connected to a light source control signal transmission line 54. A synthesis shield line of the transmission line 54 is one-point-connected to the lug 52.

The connector member 53 is, as illustrated in FIG. 1, connected to an automatic light control circuit 55 incorporated in the light source 3. Inputted to the automatic light control circuit 55 are the video signals within the CCU 4 through the cable 23 and the connector 24 connected to the connector receiver 22 of the light source connector 12. For example, the luminance signals generated by the preprocess circuit 33 shown in FIG. 2 are inputted via the light source control signal transmission line 54 to the automatic light control circuit 55. For instance, a mean value during one frame period of the luminance signal is compared with a set level to obtain an error signal. The automatic light control is performed by controlling a diaphragming quantity of the diaphragm 15 by use of the error signal.

As illustrated in FIG. 4, a net tube (also referred to as a braid) 56 is formed by knitting a metal wire in a meshing configuration. The intubation member 8 of the electronic scope 2a is provided with the net tube 56 to cover the light guide 13 and the transmission lines 21a and 21b. One end of a lead wire 57 is connected to a rear end (proximal end) of the net tube 56. The lead wire 57 is inserted through the universal cable 11. The other end of the lead wire 57 is connected to an unillustrated pin fitted to the connector 12.

Formed in the electronic scope 2 is a channel 65 which permits passing of a forceps or a treatment tool such as a high frequency electric mes (knife) 59 for incising an unnecessary part by flowing a high frequency current into the affected part. The treatment tool can be intubated from an intubation port in the vicinity of the manipulation unit 9.

The connector 24 is formed with an opening into which the sheath frame of the connector receiver 22 is substantially fitted. The connector 24 is detachably attached to the connector receiver 22 mounted on the connector 12 of the electronic scope 2. A shield gasket 61 is fitted to the inner periphery of the opening, with the result that a contact resistance between the connector receiver 22 and the sheath frame is reduced. The shield gasket 61 is molded to assume a leaf-spring-like configuration by use of a thin copper plate. Thus, the gasket 61 is surely brought into contact with the sheath frame.

The signal cable 23 has the lines which are, as in the same way with the universal cable 11, shielded by the shield cover wires for every signal system. A connector 25 is attached to the other end of the cable 23. The connector 25 is also provided with a shield gasket 62 for making sure a contact with a cylindrical frame (marked with a symbol 81a in FIG. 8) of a connector receiver 26.

Figure 6:
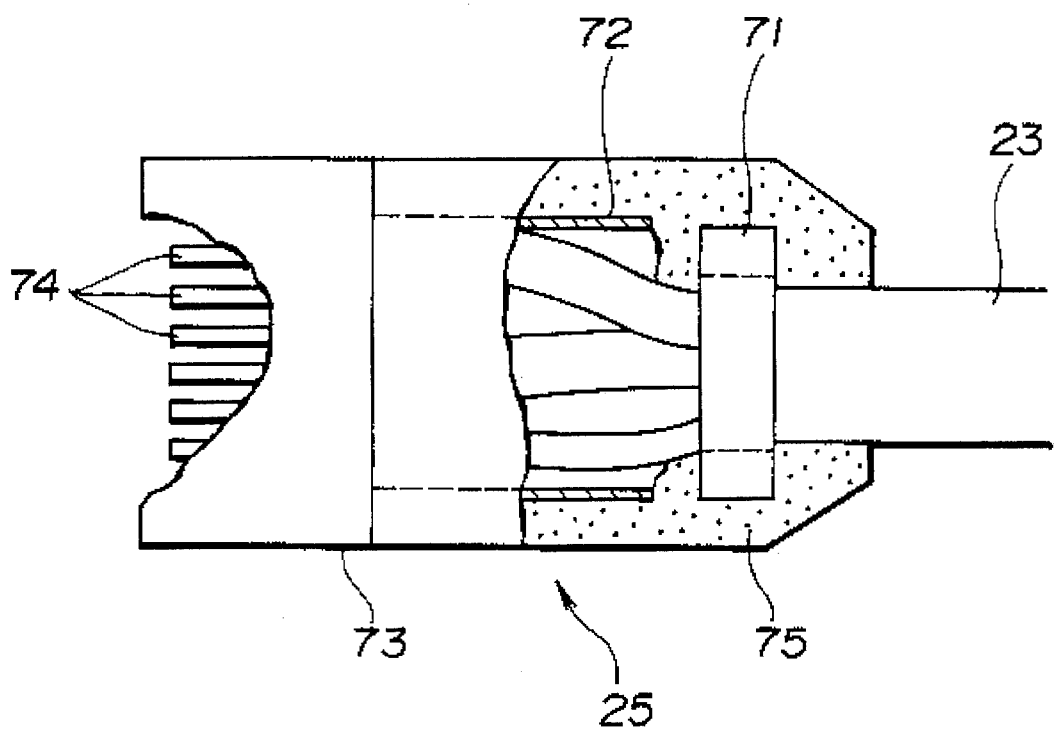
Figure 7:
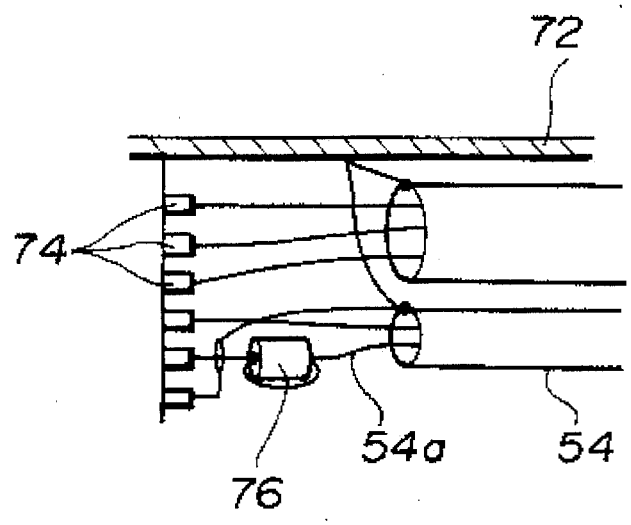

As depicted in FIG. 6, a ring-like ferrite member 71 fixedly housed in the connector 25 is set at the end of the signal cable 23. The respective signal conductors are connected to the proximal ends of pins 74, 74, ... of a connector body 73 via a metal cylinder 72. The individual shield cover wires of the transmission lines 21a, 21b, ... are, as illustrated in FIG. 7, connected to the metal cylinder 72. A resin 75 is mold-fixed to the periphery of the ring-like ferrite member 71 serving as an impedance element for increasing an AC impedance as well as to an outer periphery of the metal cylinder 72. The ring-like ferrite member 71 works to absorb and attenuate the noises leaked out of the transmission lines 21a, 21b, ..., thus reducing the generation of the radiant noises. In this case, when encasing the ring-like ferrite member 71 into the metal cylinder 72, a metallic portion including the metal cylinder 72 transmits the noises. To prevent the transmission thereof, the ring-like ferrite member 71 is provided apart from the metal cylinder 72.

As illustrated in FIG. 7, the control signals are transmitted through a transmission line 54 which connects the CCU 4 to the light source 3. The transmission line 54 includes a light quantity control signal line 54a for transmitting, e.g., light quantity control signals. Only this signal line 54a is connected via a small-sized ring-like ferrite member 76 to the pin 74 inwardly of the metal cylinder 72. Because of passing though this ring-like ferrite member 76, the signals of the signal line 54a typically assume a lower level. This prevents the signals from being easily influenced by the noises.

A shield wire of the signal line 54a (the shield wire of a coaxial line, i.e., the signal line 54a) is connected to the shield cover wire of the transmission line 54.

Figure 8:
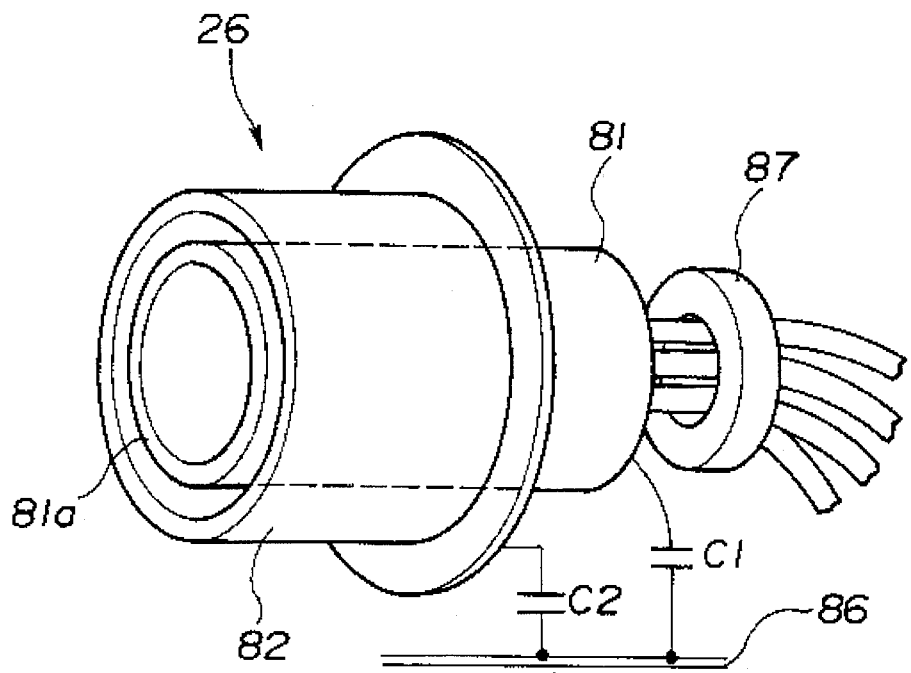
Figure 9:
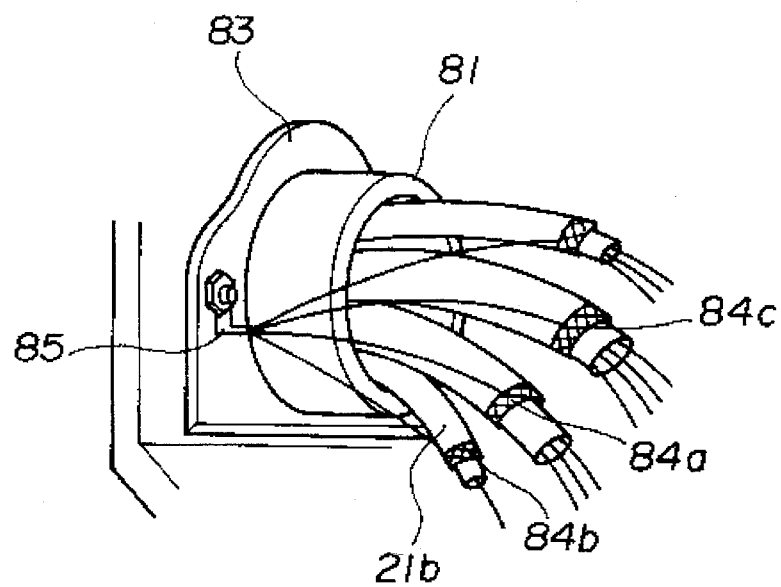

The connector receiver 26 of the CCU 4 to which the connector 25 shown in FIG. 6 is connected is configured in a double cylindrical structure. In this structure, as illustrated in FIG. 8, a cylindrical frame 81a is provided at the front end of a metal connector receiver body 81. A reinforcement cylindrical metal frame 82 encompasses the cylindrical frame 81a in such a way that the frame 82 is insulated from the body 81. The connector receiver body 81 is, as illustrated in FIG. 9, conductive to a connector receiving fixing conductor 83 connected to GND of the patient circuit 30 on the rear side thereof. Referring again to FIG. 9, as in the same way with the transmission lines 21a, 21b, ... within the cable 23, connecting lines led out from the connector receiver body 81 to the CCU 4 are shielded by synthesis cover wires 84a, 84b, 84c ... for every signal system. The respective shield cover lines 84a, 84b, 84c, ... are connected via lead wires to a lug 85 of the conductor 83. More specifically, the shield cover wires 84i (i =a, b, c, ... ) are one-point-connected to GND of the patient circuit 30, thereby preventing the generation of unnecessary radiant noises. The one-point-connection serves to prevent the generation of noises, which are originally caused due to a difference in potential when forming a current path in the case of providing no one-point-connection.

As shown in FIG. 8, the metallic portion of the connector body 81 is connected via a capacitor C1 serving as an impedance element to a chassis 86 conceived as GND of the secondary circuit 35, thus providing an AC conduction. An external metal frame 82 is connected via a capacitor C2 to the chassis 86. The metal frame 82 serves as an antenna which works to restrain the generation of unnecessary radiant noises. To be specific, if no capacitor C2 is provided, the metal frame 82 stands afloat from GND of the secondary circuit 35. The radiation of the futile electric waves from the metal frame 82 is effected easily. Besides, the noises tend to intermix. The metal frame 82 can, however, be held AC-wise at an impedance as low as GND of the secondary circuit 35 owing to the capacitor C2. The futile electric waves are made to flow towards the chassis 86, thereby reducing the level of radiant noises.

Each of the capacitors C1 and C2 has a proof pressure of, e.g., 4 kV or more. Each of the capacitors employed herein has a capacity of, e.g., 680–1000 pF. The capacitors C1 and C2 are arranged to satisfy the conditions under which an insulating deterioration is not caused even when applying high pressures to GNDs of the patient circuit 30 and of the secondary circuit 35.

As illustrated in FIG. 8 (or FIG. 1), the connector receiver 26 is arranged to decrease the generation of noises by, as in the same way with the connector 25, causing the wires to pass through a ring-like ferrite member 87. (Illustration is omitted in FIG. 7.) This ring-like ferrite member 87 is effective in eliminating the noises which permeate in a common mode. The capacitor C1 assists the action of the ring-like ferrite member 87.

Figure 10:
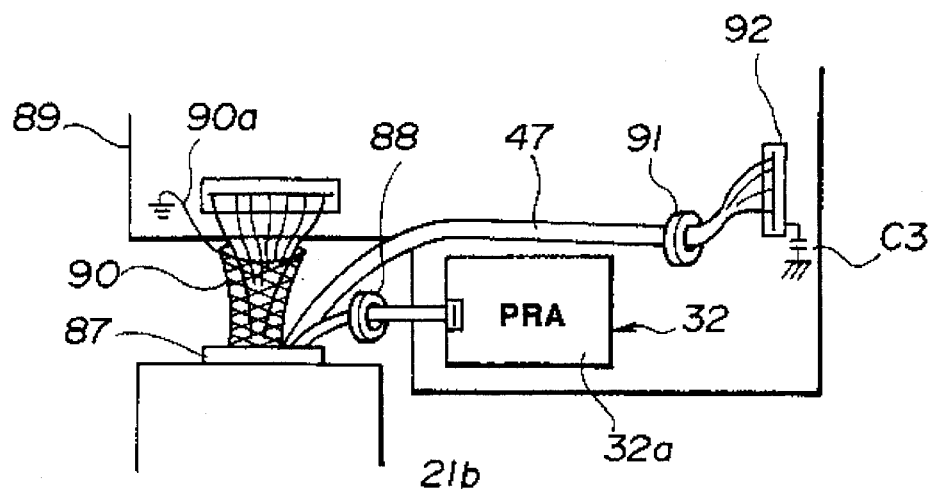

As depicted in FIG. 1 or 10, the CCD output signal transmission line 21b passes through a ring-like ferrite member 88 to prevent the generation and intermixing of noises. The CCD output signals are thus inputted to a preamplifier 32. Since the feeble CCD output signals are inputted to the preamplifier 32, unlike other components of the patient circuit 30, a shield case 32a encases the preamplifier 32 to prevent intermixing of noises to the greatest possible degree.

As illustrated in FIG. 10, the transmission line 21a of the CCD driving system is connected via the ring-like ferrite member 87 to a connector receiver of a mother board 89 of the patient circuit 30. The transmission line 21a is entirely wound with a copper tape 90, thus shielding the line 21a. The copper tape 90 is connected via a lead wire 90a to GND of the patient circuit 30, and the generation of noises is thereby prevented. Namely, the ends of the respective signal lines connected to the connector receiver are scattered enough to cause insufficient shielding. The noises tend to be circumfused from the ends thereof. The generation of noises is, however, restrained by forming the shield means in the manner described above.

A connector 92 is, as depicted in FIG. 10, secured via a ring-like ferrite member 91 to the end of the control signal transmission line 47. The connector 92 is connected to a connector receiver of the mother board 89. In the mother board 89 positioned closer to the connector receiver, the transmission line 47 is connected via a bypass capacitor C3 to GND of the patient circuit 30. (In FIG. 3(a) also, the signal line 47b is connected via the capacitor C3 to GND.)

As described above, horizontal transfer clocks are transmitted for driving, e.g., the CCD in the electronic scope 2. For this reason, the clocks conceived as noise are easily intermixed in the control signal transmission line 47. Besides, the noises tend to be released outside via the transmission line 47. In contrast, however, the transmission line 47 is connected via the capacitor C3 to GND, thereby producing a large effect in reducing the radiant noises. Note that the capacitor C3 usable herein is formed of ceramic or tantalum to have a capacity of, e.g., 0.1 µF.

It should be also noted that a CCD driving line of a board (indicated by the symbol 31a of FIG. 1) formed with the CCD driver 31 in the patient circuit 30 is arranged to restrain the noises from being generated in the circumference through a lead ferrite member (not shown). Referring again to FIG. 10, the control signal transmission line 47 is separated from the transmission line 21a of the CCD driving system. As illustrated in FIG. 1, however, there is made a connection to a common connector receiver of the mother board 89 by use of a common connector. In this case, as shown in FIG. 1, there may be made a connection to GND of the patient circuit 30 through the capacitor C3 in the vicinity of the end at which the CCD driving signal is outputted in a position close to the connector receiver. With this arrangement, the CCD driving signal is capable of effectively preventing the noises from being circumfused through the control signal transmission line 47.

Figure 11:
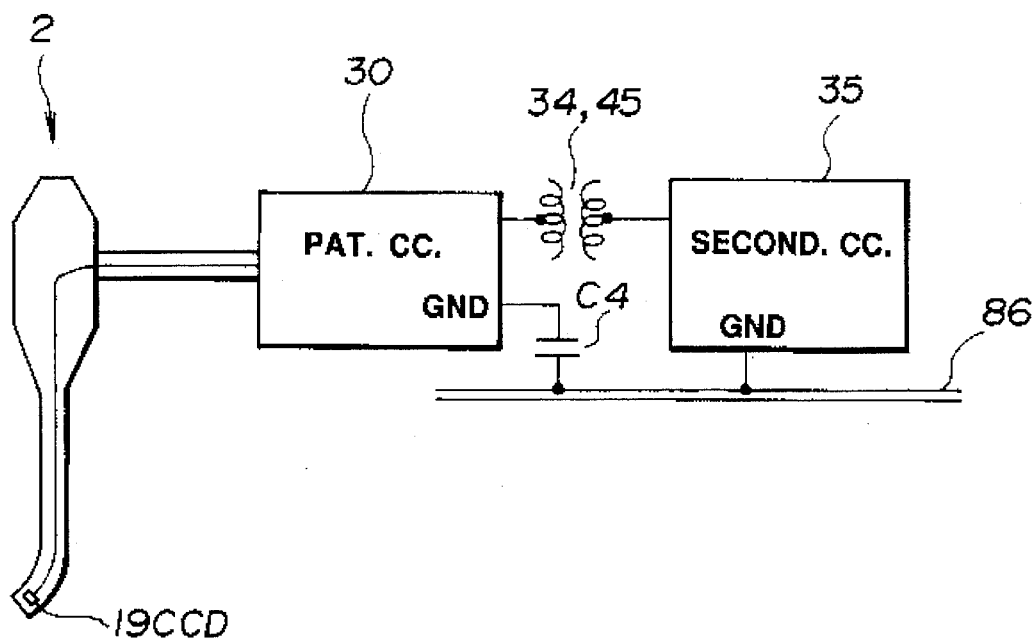

As shown in FIG. 1, or 2 or 11, GND of the patient circuit 30 is connected AC-wise to GND of the secondary circuit 35 through an impedance element, i.e., a capacitor C4. The capacitor C4 is durable against a proof pressure of, e.g., 4 kV. The capacitor C4 serves to reduce an impedance between GNDs of the patient circuit 30 and the secondary circuit 35 especially at higher frequencies. In a high frequency zone, the capacitor C4 directly connects two GNDs to each other, thereby exhibiting a function approximate to that of GNDs which are made common.

Hence, high frequency signals handled in the patient circuit 30 or the secondary circuit 35 are easily radiated outside through a small floating capacity particularly in the high frequency zone. GNDs of the two circuits 30 and 35 are AC-wise connected to each other via the capacitor C4. A large proportion of currents which are to be radiated can be dropped down to GNDs.

For this reason, the unnecessary electric waves are radiated, whereby the emissions to other circuits and the outside can remarkably reduced. In addition, the high frequency noises are easy to permeate from outside via the floating capacity. It is, however, possible to equivalently decrease the impedance with respect to GND at the noise-permeated portion. Most of the noises are dropped down to GNDs, as a result of which a rate of intermixing in the signal system can be lowered.

Note that this arrangement is effective as a countermeasure against EMC (a generic name of EMI (a problem of causing an electromagnetic interference) and EMS (a problem of undergoing the electromagnetic interference)) owing to the capacitor C4 having a large capacity. However, a leakage current increases, so that the capacity is appropriately set corresponding to the environment in the actual circuit system.

As shown in FIG. 1, a mother board 93 includes a CPU which mainly constitutes the controller 39. A flat cable 94 is provided for connecting the mother board 93 to the secondary circuit 35. A countermeasure against the noises is taken also in the flat cable 94 through a ferrite core 95. A flat cable 97 is connected to a front panel 96 in the mother board 93. The flat cable 97 is arranged to reduce the noises through a ferrite core 98. A cable 101 is connected to a connector receiver 100 to which a connector fitted to a cable 99 of the TV monitor 5 is connected. The cable 101 is likewise arranged to reduce the noises through a ferrite core 102.

Figure 12:
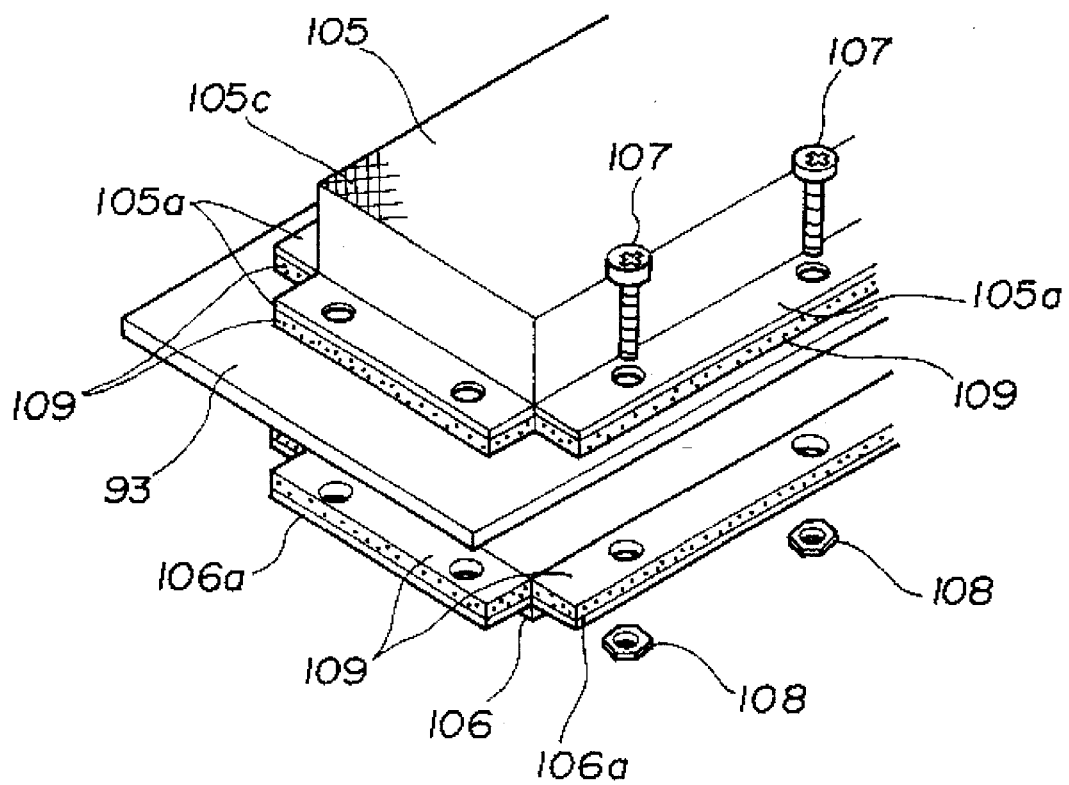

The mother board 93 depicted in FIG. 1 is, as illustrated in FIG. 12, shielded with shield cases 105 and 106.

More specifically, the shield case 105 covers a part surface (upper surface) on which the parts of the mother board 93 are packaged, while the shield case 106 covers the lower surface thereof. Fitting pieces 105a, ..., 106a, ... (to the mother board 93) of the shield cases 105 and 106 are fixed to the mother board 93 by using screws 107, ... and nuts 108. In this case, an enhancement of the shield function involves the following arrangement. A rubber-like gasket member 109 exhibiting an elasticity and conductivity is fixedly interposed between the fitting piece 105 or 106 and the mother board 93.

The gasket member 109 interposed therebetween acts as follows. When the adjacent screws 107, 107 are fixed in a distant position, and even if the fitting piece 105a is fixed to the mother board 93 so that they are not in close contact with each other, a press-deformation of the gasket member 109 works to diminish a gap. Shielding can thus be effected with a certainty.

Figure 13:
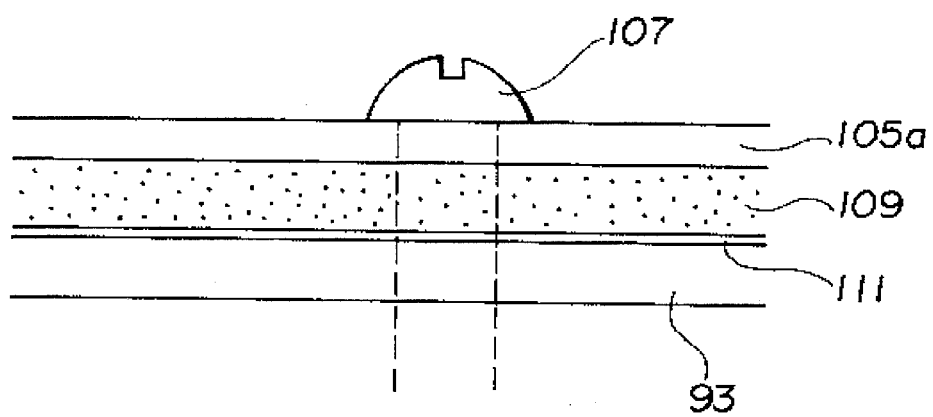

The fitting pieces 105a and 106a are provided long on the peripheries of the openings of the shield cases 105 and 106 to decrease disconnected portions thereof. A GND land 111 is formed as long as possible on the mother board 93 confronting with the fitting pieces 105a and 106a. Therefore, as illustrated in FIG. 13, the fitting portions—e.g., the fitting piece 105a of the shield case 105, the gasket member 109, the GND land 111 formed on the mother board 93 and the mother board 93 itself—are laminated. In the diminished-gap state by the shield cases 105 and 106, both surfaces of the mother board 93 are shielded. It is therefore feasible to minimize both an emission of noises to the outside and intermixing thereof from the outside.

The CCU 4 illustrated in FIG. 1 includes a box. A lower part of the box is formed with weep holes through which the water permeated into the CCU is wept out. In the conventional example, there was no contrivance to restrain the noises from being radiated outside via the weep holes in this case. In accordance with this embodiment, however, the weeping function can be kept by providing configurations shown in FIGS. 14a to 14d. At the same time, the noise radiation can also be restrained.

Figure 14:
Figure 14:
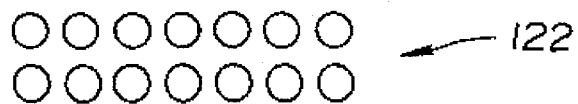
Figure 14:
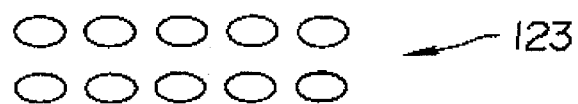
Figure 14:

FIG. 14a illustrated a weeping member 121 formed by meshing a metal wire. In this case, a mesh size (the maximum length in the mesh) is set smaller than a wavelength of the highest frequency dealt with inside the CCU 4. This configuration sufficiently prevents the noise radiation and noise permeation as well. FIG. 14b depicts a weeping member 122 having a multiplicity of small circular holes formed in a metal bottom plate. A size of the small hole may be set as in the same way with the mesh. FIG. 14c shows a weeping member 123 formed with small elliptic holes. FIG. 14d illustrates a hole formed by rounding the corners of a rectangle. With this arrangement, a magnitude of noise radiation becomes smaller than in the conventional example where the corners thereof are not rounded.

Note that the shield cases 105 and 106 shown in FIG. 12 may have the configurations shown in FIG. 14a. For instance, the shield case 15 is composed of a metal wire 105c knitted in mesh. By virtue of this arrangement, the weight can be reduced. For example, this arrangement is applicable to a case where the patient circuit is shielded by the shield case and further to shielding of a circuit board.

Figure 15:
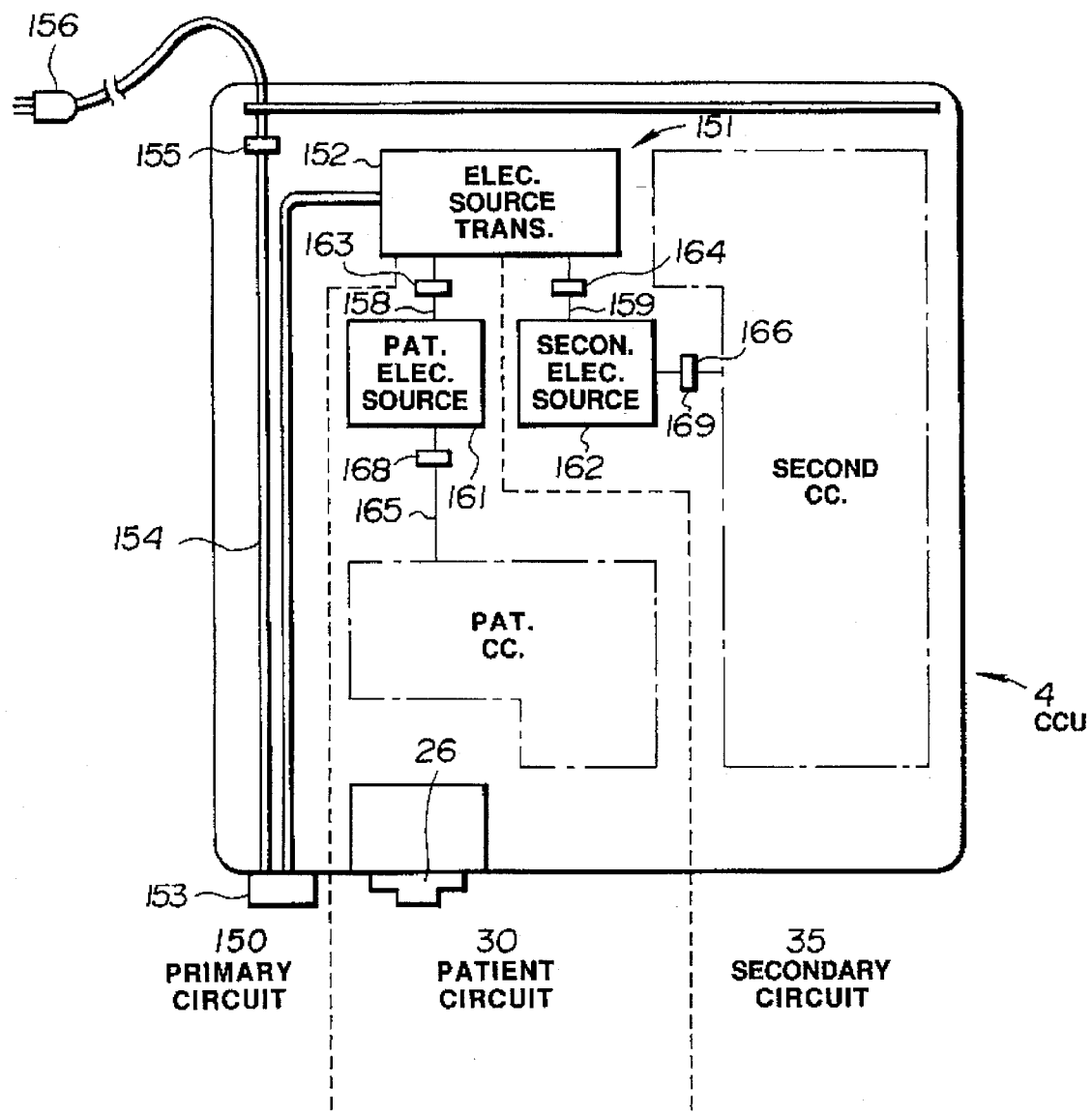

FIG. 15 illustrates an electric source unit 151 in which the patient circuit 30 and the secondary circuit 35 are isolated from a primary circuit 150.

Connected to a main switch 153 is a cable connected to a primary winding of an electric source transformer 152 encased in the case of the CCU 4. An AC cable 154d led outside from the main switch 153 passes through a ring-like ferrite member 155 for preventing emission/permeation of the conduction noises within the case. An AC plug connected to a terminal of the AC cable 154 is connected to an unillustrated commercially-available electric source plug socket. Commercial AC power is thus supplied to the electric source transformer 152.

The conduction noise herein implies a noise traveling through the AC cable 154 and flowing into the plug socket to which the plug 156 is connected. This kind of noise flowing through AC cords of other devices connected to the same plug socket and exerts adverse influences on those devices.

An earth wire of the cable 154 is connected to a chassis 87.

The primary circuit 150 on the side of the commercial electric source is isolated from a secondary winding by the electric source transformer 152. The primary winding of the transformer 152 is supplied with the AC voltage to induce predetermined AC voltages in two secondary windings. The electric power is fed via the cables 158 and 159 to a patient electric source circuit 161. These cables 158 and 159 pass through ring-like ferrite members 163 and 164 for preventing an inflow of noises.

The patient electric source circuit 161 and the secondary electric source circuit 162 generate predetermined DC voltages. The electric power is supplied via cables 165 and 166 to the patient circuit 30 and the secondary circuit 35 as well.

These cables 165 and 166 pass through ring-like ferrite members 168 and 169 for preventing the inflow of noises.

Figure 16:
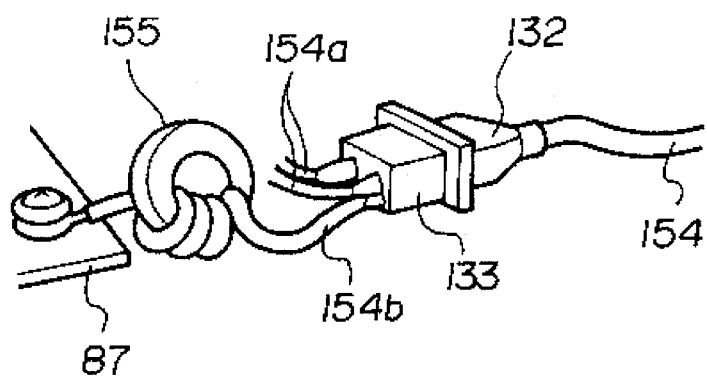
FIG. 16 is a perspective view depicting a connecting unit to a commercially available electric source.

Incidentally, in FIG. 15 the whole cable 154 passes through the ring-like ferrite member 155. As illustrated in FIG. 16, however, the earth wire 154b is provided together with, e.g., two feeder lines 154a constituting the cable 154. This earth wire 154b passes through the ring-like ferrite member 155 and may be connected to the chassis 87 provided inwardly of the box (case). In this case, a ring-like ferrite member 154 is wound with several turns of the earth wire 154b which is then connected to the chassis 87. The noises are thus restrained from permeating from outside via the earth wire 154b into the CCU 4. Simultaneously, the noises are restrained from being released outside. Referring to FIG. 16, the AC cable 154 is fitted with the AC plug 156. The cable 154 is connected to the AC cable 154 within the case through an inlet 133 attached to the case as well as through the plug 132. Note that a switching regulator or an AC-DC converter for transforming the commercial voltage is usable in place of the electric source transformer 152.

In the electronic endoscope system 1 in the first embodiment discussed above, the electronic scope 2 is intubated into the body cavity and employed therein. The CCU 4 insulates the patient circuit 30 connected to the CCD 19 within the electronic scope 2 from the secondary circuit 35 for effecting signal processing to output the video signals to the TV monitor 5. The safety is secured as in the same way with the conventional example.

In this case, the secondary circuit 35 is connected to the earth, whereby the shield function can be enhanced. However, GND of the patient circuit 30 can not be conductive to GND of the secondary circuit 35. In the conventional example, the shielding function is insufficient. In accordance with the first embodiment, however, as explained earlier, it is possible to reduce the noises radiated and flowed outwardly of the system. Besides, the noise permeation from the external units can sufficiently be decreased. It is because the respective units are provided with the means for reducing or restraining the radiation/permeation of noises and also the inflow of the conduction noises.

Hence, the clear-cut endoscope image can be obtained without undergoing the influences by the noises. In addition, the malfunction is not caused due to the noises. The system with high safety can be attained. Besides, the noise radiation.outflow towards the external units can sufficiently be reduced. Even when simultaneously using the external units, the original functions are not deteriorated, and the malfunction incidental to the noises does not happen.

Shielding is carried out between different signal systems in the endoscope system 1. In consequence, the functions of the respective signal systems are well exhibited within the endoscope system 1. The sharp endoscope image is thereby obtainable.

In this embodiment, the patient circuit 30 and the secondary circuit 35 are isolated from the commercial electric source by the primary circuit 150. If a fault happens, the high safety can be secured.

Figure 17:
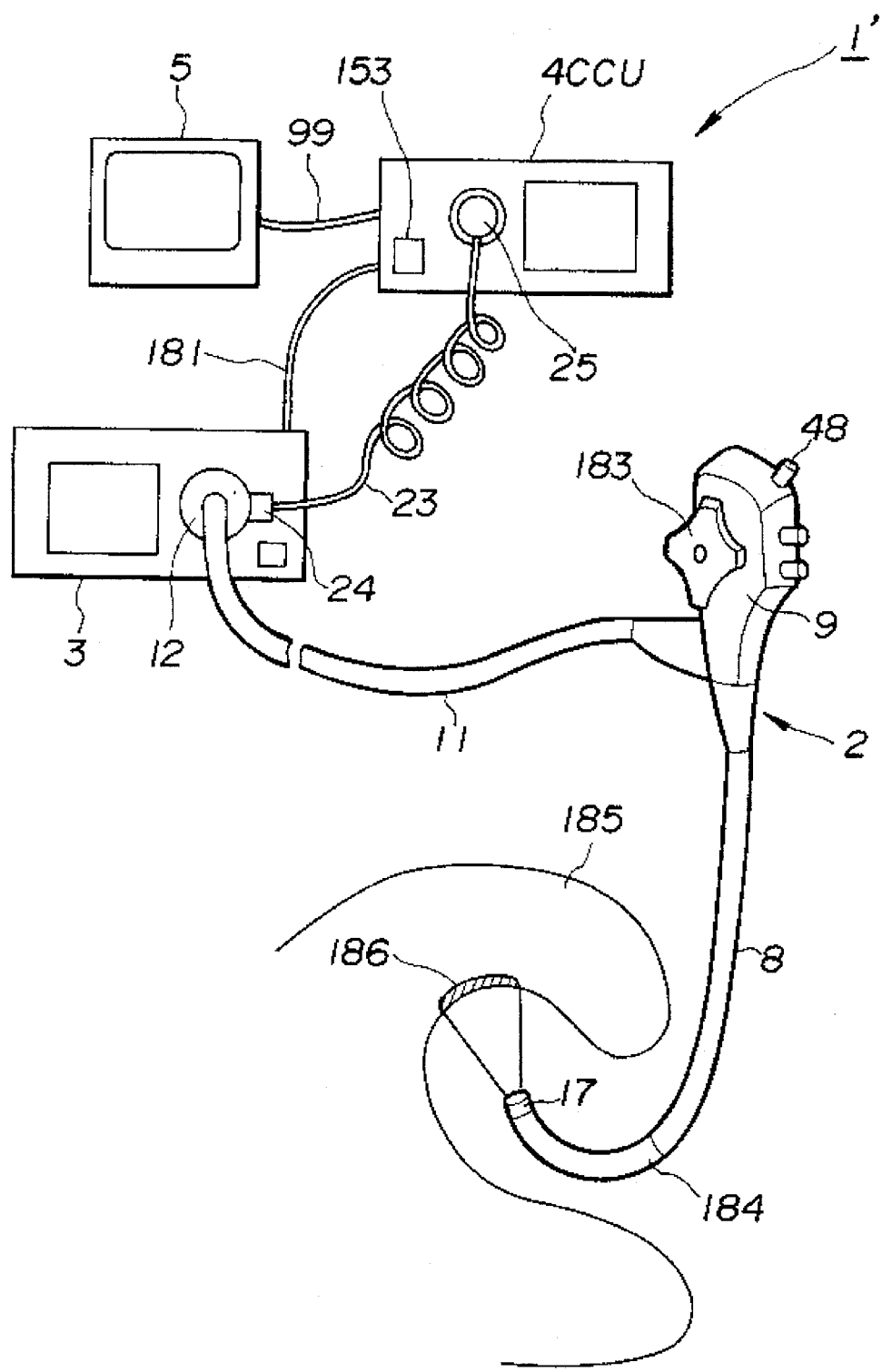
FIG. 17 is an explanatory view showing a variant form of the first embodiment of the invention.

FIG. 17 illustrates a whole construction of an electronic endoscope system 1' in a variant form of the first embodiment of this invention.

In the first embodiment, the control signals are transmitted between the CCU 4 and the light source 3 via the control signal transmission line 54 inserted through the cable 23. As shown in this variant form, the control signals may be transmitted between the CCU 4 and the light source 3 via a communications line 18 provided outwardly of the cable 23.

Referring to FIG. 17, a bending manipulation knob 183 is mounted on the manipulation unit 9 of the electronic scope. A bending member 184 adjacent to the tip thereof is bendable. When inserting an intubation unit 8 into a body cavity 185, a tip 17 can be set in such a direction as to facilitate an observation into a target effected part 186.

Other constructions are the same as those in the first embodiment. The same components are marked with the like symbols, and the description thereof is omitted herein.

FIG. 18 illustrates the principal portion of an electronic endoscope system 201 in a second embodiment of this invention.

The second embodiment is fundamentally configured by adding an electric knife device 202 to the construction of the first embodiment.

The electric knife 59 is inserted in a channel of the electronic scope 2. The electric knife 59 is connected via a lead wire 203 to a terminal A of an electric knife device 202. A connector 12 of the electronic scope 2 is connected to the light source 3. A cable 205 is provided with a connector 204 connected to a terminal provided on the side portion of the connector 12. The connector 12 is connected via the cable 205 to a CCU 4'. The CCU 4' includes a connector receiver 207 fitted with a connector 206 secured to the other end of the cable 205.

The connector receiver 207 is connected to a common contact point c of a switch 208. A contact point a is connected to GND of the patient circuit 30. A lever of the switch 208 is normally, as illustrated in FIG. 19, biased by a spring 209 to turn ON the contact point a.

On the other hand, when mounting a pin 212 of a connector 211, the pin 212 presses the lever to turn OFF the contact point a. At the same time, the pin 212 is connected to a contact point c.

The connector 211 is connected to a terminal S of the electric knife device 202 through a connector 214 disposed at the other end of the cable 213.

The terminal S is connected via a capacitor to one end of a transformer 215. The other end of the transformer 215 is connected via a capacitor to the terminal A. One end of the transformer 215 is connected via a capacitor to the terminal S. The primary side of the transformer 215 is connected to a high frequency output circuit 216. A high frequency outputted from the high frequency output circuit 216 is supplied via the transformer 215 to the secondary side.

A terminal P is connected via a lead wire 217 to a plate 219 which widely contacts the body face of a patient 218. On the other hand, an electrode inserted through a sheath 221 of the electric knife 59 is protruded from an opening formed at the top end of the sheath 221. With this arrangement, a loop 222 is allowed to be caught by a polyp 223. When a foot switch 224 is turned ON, the high frequency is outputted from the high frequency output circuit 216 under control of a control circuit 225 connected to this switch 224.

Inputted to the control circuit 225 are output signals of current transformers 226 and 227 for detecting the currents flowing to the terminals P and A. A ratio of IP/IA of the currents flowing in the terminals P and A is detected. If the level ratio of IP/IA is larger than a set value, a "constant percentage" or more of the high frequency current IA flowing out via the terminal A passes through the plate 29 and returns to the terminal P. An amount of current flowing in other portions than this route is small. This may imply a normal working state.

Namely, as illustrated in FIG. 18, the high frequency current flows from the electric knife via the terminal A to the patient 218. At this time, a leakage current, more or less, flows through a braid 56 and a terminal S depending on a floating capacity with respect to the braid 56 defined as a conductive member peripheral to the electric knife 59 in some cases.

Considering a magnitude of the leakage current depending on the floating capacity, a prerequisite step is to examine a value, corresponding to the leakage current, by which the current IP is smaller than the current IA. A value of the above-mentioned level ratio is set for a comparison with a level ratio detected during the actual use. Whether the working state is normal or not can be thus judged. If smaller than the set value, an alarm is given by an alarming device 228 such as a buzzer.

The connector 214 is provided with a pin 231 for detecting whether or not the connector 214 is connected to the electric knife device 202. When connecting the connector 214 thereto, the pin 231 presses a switch lever 233, resisting an elastic force of the spring 232. The contact points a and b are thereby turned ON. When the control circuit 225 detects this ON-state, the high frequency output circuit 216 outputs the high frequency immediately when turning ON the foot switch 224.

In this embodiment, where no treatment is made by use of the electric knife 59, the connector 211 is not connected. Hence, the contacts points a and c of the switch 208 are turned ON. In consequence, the braid 56 of the electronic scope 2 remains connected to GND of the patient circuit 30. The braid 56 contributes to a reduction in noises.

On the other hand, where the treatment is performed with the electric knife 59, the connector 211 is connected. The switch 208 is therefore turned OFF with the aid of the pin 212. In this case, the braid 56 is available for detecting the leakage current caused when using the electric knife. Other constructions are the same as those of the first embodiment.

In accordance with the second embodiment, if no electric knife 59 is employed, the braid 56 is connected to GND of the patient circuit 30. This is effective in decreasing the generation of noises.

Whereas if the knife 59 is employed, the braid 56 is made non-conductive to GND, and thereafter the leakage current is detectable. The treatment can be effected with the electric knife 59 having the high safety. Other effects are the same as those of the first embodiment.

Note that as illustrated in FIG. 3b, the electric source terminals Vc1 and Vc2 of the patient circuit 30 and the secondary circuit 35 are connected to GNDs through the capacitors C and C' each having the large capacity. For instance, the capacitor C4 may be connected not to GND but between the electric source terminals Vc1 and Vc2. Besides, the capacitor C4 may be connected between GND of the patient circuit 30 and the electric source terminal Vc2. This is apparently applicable to another capacitor C1.

Note that this invention is applicable to a system in which a fiber scope in place of the electronic scope 2 is mounted with a TV camera.

Figure 20:
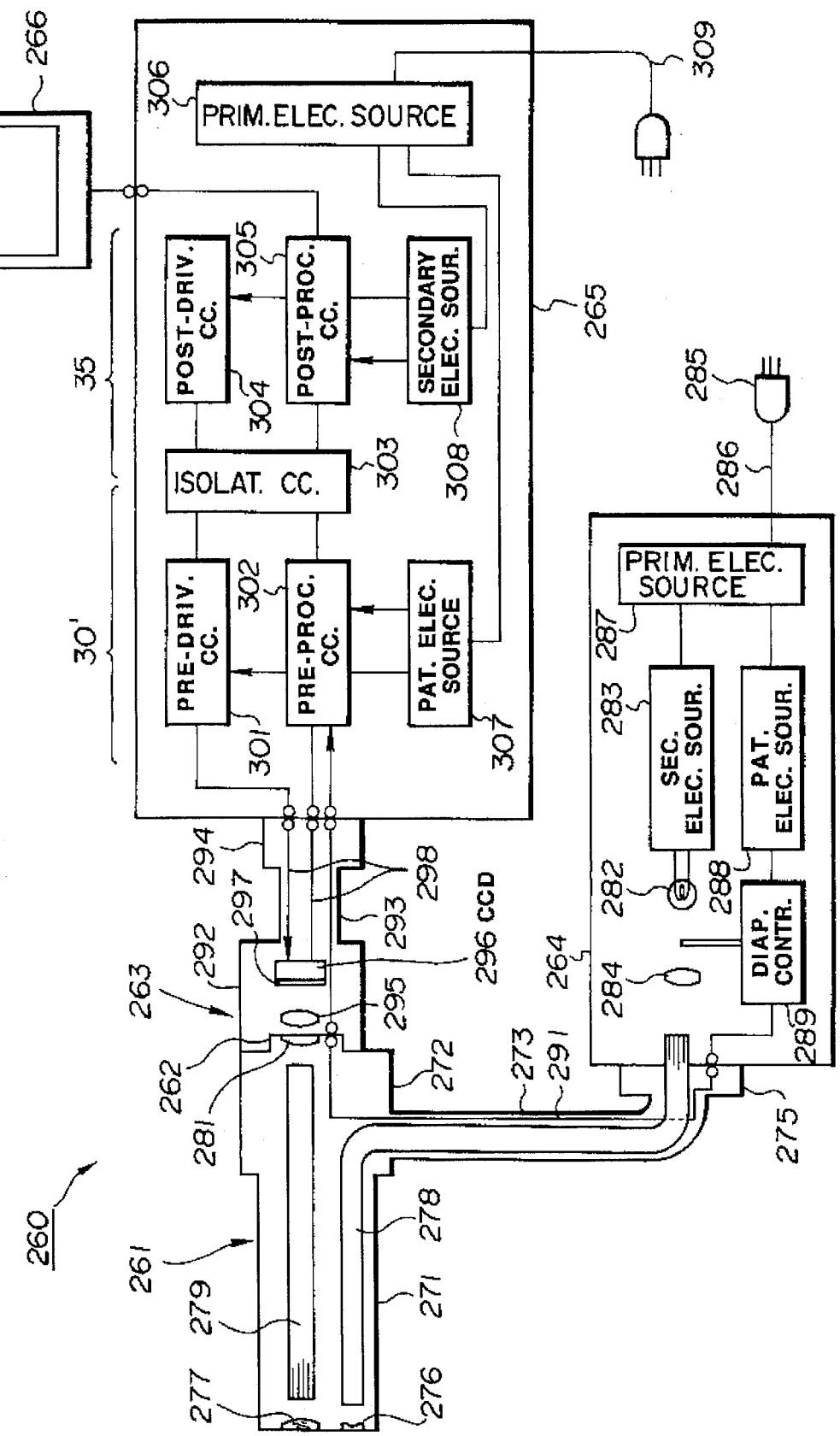
FIG. 20 is a block diagram showing a third embodiment of this invention.

FIG. 20 illustrates a whole construction of an electronic endoscope system 260 in a third embodiment of this invention.

The third embodiment will deal with an example of an external attachment type endoscope system including an externally attached TV camera 263 connected to an ocular unit 262 of a fiber scope 261.

As depicted in FIG. 20, the electronic endoscope system 260 comprises: the fiber scope 261; a light source 264 to which this fiber scope 261 is connected; the external attached TV camera 263 connected to the ocular unit 262 of the fiber scope 261; a CCU 265, separate from the light source 264, to which the TV camera 263 is connected; and a CRT monitor 266 connected to the CCU 265.

The fiber scope 261 includes an elongate intubation unit 271 exhibiting a flexibility; an manipulation unit 272; the ocular unit; a light guide cable 273; and a connector 275.

The manipulation unit 272 is provided in continuation from the rear end of the intubation unit 271. The ocular unit 262 is disposed at the rear end of the manipulation unit 272. The light guide cable 273 extends from the manipulation unit 272. The connector 275 is provided at the end of the light guide cable 273 and detachably connected to the light source 264. The tip of the intubation unit 271 is provided with a light distribution lens 276 and an objective lens 277. A light guide fiber 278 is led from the rear end of the light distribution lens 276. The light guide fiber 278 is inserted through the intubation unit 271, the manipulation unit 272 and the light guide cable 273. An incident end of the fiber 278 is connected to the connector 275. The top end face of an image guide fiber 279 is disposed in an image forming position of the objective lens 277. The image guide fiber 279 is inserted through the intubation unit 271 as well as through the manipulation unit 272. The rear end face of the fiber 279 confronts with an ocular lens 281 incorporated in the ocular unit 262.

The light source 264 consists of: a lamp 282; a secondary electric source circuit 283 for feeding the electric power to the lamp 282; and a lens 284 for condensing beams of light emerging from the lamp 282 and making the light incident on an incident end of the light guide fiber 278. The secondary electric source circuit 283 is insulated from the commercial electric power by a primary electric source circuit 287 to which an AC cord 286 having its terminal connected to an AC plug 285 is connected. The predetermined electric power is thus supplied. The primary electric source circuit 287 functions to insulate a patient electric source circuit 288 from the commercial electric power, thus supplying the predetermined electric power. The patient electric source circuit 288 supplies the driving electric power to a diaphragm control circuit 289 for controlling an amount of illumination light. EE signals for controlling the illumination light quantity are transmitted from a CCU 265 via a signal cable 291 inserted through the light guide cable 273 to the diaphragm control circuit 289.

The TV camera 263 comprises: a camera head 292 detachably connected to the ocular unit 262; a cable extending from the camera head 292; and a connector 294 provided at the end of the cable 293 and detachably connected to the CCU 265. The camera head 292 incorporates an image forming optical system 295 for forming an image observed from the ocular unit 262 and a CCD 296 disposed in an image forming position of this optical system 295. A color filter 297 for separating the colors is disposed on a light receiving surface of the CCD 296.

A signal line 298 for transmitting the driving and output signals is connected to the CCD 296. The signal line 298 is connected to the connector 294 inserted through the cable 293.

The CCU 265 is connected via the signal line 298 to a pre-drive circuit 301 and to a preprocessing circuit 302. The pre-drive circuit 301 and the preprocess circuit 302 are connected via an isolation circuit 303 to a post-drive circuit 304 and a post-process circuit 305, respectively. The CCU 295 accommodates a patient electric source circuit 307 and a secondary electric source circuit 308. These circuits 307 and 308 are supplied with voltages insulated from the commercial electric power by the primary electric source circuit 306. The patient electric source circuit 307 feeds DC power of a predetermined voltage to the pre-drive circuit 301 and the preprocess circuit 302. The secondary electric source circuit 308 feeds the DC power of a predetermined voltage to the post-drive circuit 304 and the post-process circuit 305. A secondary winding of the primary electric source circuit 306 is supplied with the electric power from the commercial electric source through the AC plug attached to the terminal of the AC cord 309.

For example, a luminance signal of the preprocess circuit 302 is inputted via the signal cable 291 to the diaphragm control circuit. The luminance signal is employed for controlling the light quantity.

A standard video signal generated by the post-process circuit 305 is inputted to the CRT monitor 266, whereby a subject image is displayed on the CRT monitor 266.

In accordance with this embodiment, the subject is irradiated with white illumination light emitted from the light source 264 after traveling through the light guide fiber 278 and the light distribution lens 276 as well. The subject image is formed on the top end face of an image guide fiber 279 in combination with an objective lens 277. The image is transferred via the image guide fiber 279 to the ocular unit 262. The subject image is further formed on the CCD 296 with the help of the image optical system 295 of the externally attached TV camera 263. The image undergoes a photoelectric conversion by means of the CCD 296. In this embodiment also, the isolation circuit 303 acts to isolate a patient circuit 30' from a secondary circuit 35'. The patient circuit 30' and the secondary circuit 35' are isolated from a primary circuit 150'.

In this embodiment also, there is provided a means (illustration is omitted), similar to that of the first embodiment, for reducing the noises.

Figure 21:
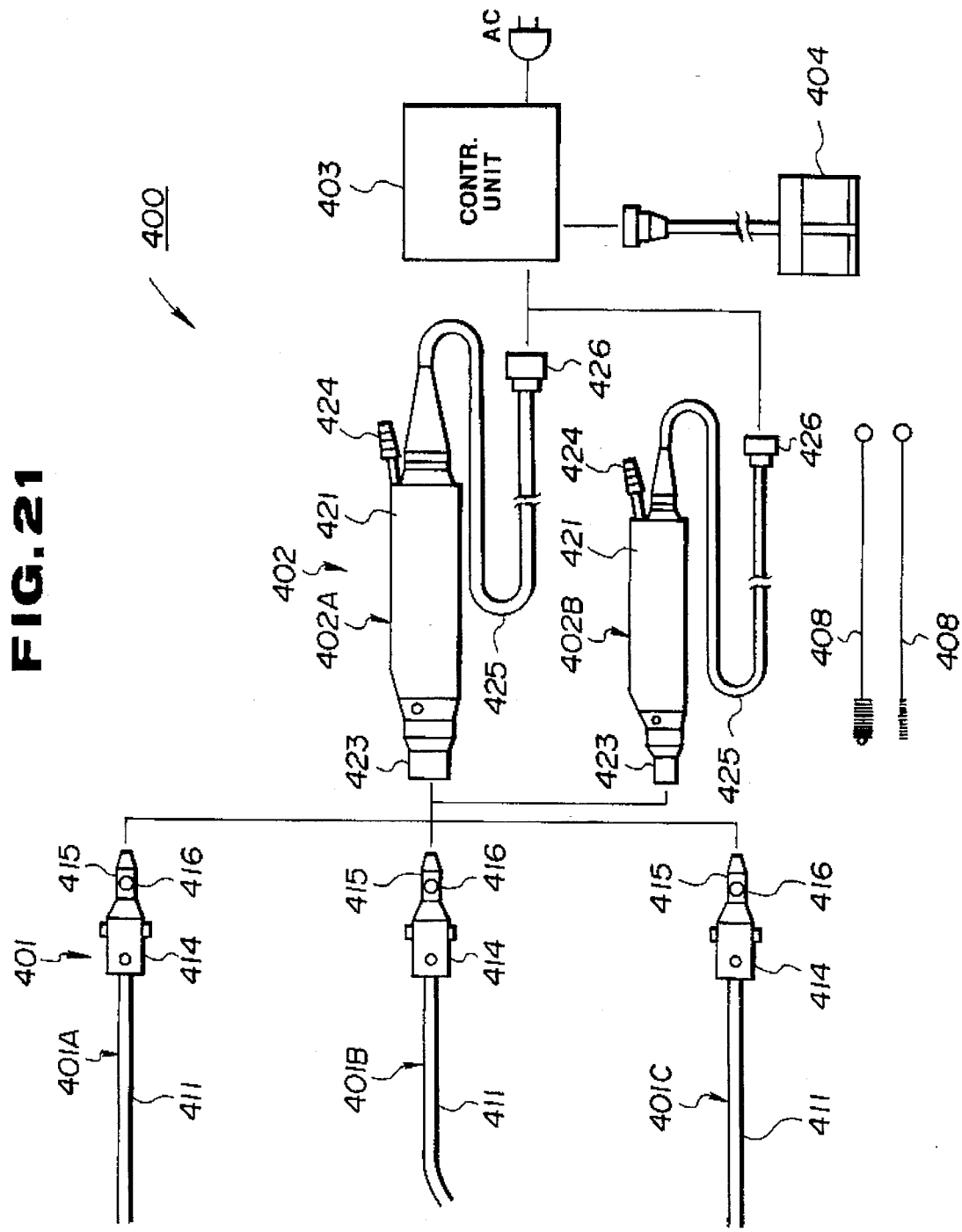
FIGS. 21 and 22 in combination show a fourth embodiment of this invention.

FIG. 21 illustrates a surgical operation system 400 in a fourth embodiment of the present invention. The surgical operation system 400 in this embodiment is provided to excise a tumor or a cartilage in a knee articulation or the like.

In an articulatory operation, for example, the tumor on the knee cover bone is excised. The damaged cartilage and bone are excised off from the knee articulation. The articulatory operation has hitherto been based on the incision method (open-cut surgery). This kind of operation, however, requires a relatively large scale incision. There is induced an external wound incidental to the incision. At the same time, this is accompanied with pains and a kinetic regulation. A complete recovery takes much time.

In recent years, a surgical operation system has been proposed. The articulation is formed with a small pierced hole under observation by use of an articulatory mirror (endoscope) without incising the articulation. An elongate cutting edge is inserted into this pierced hole to effect the operation.

This embodiment is applied to the surgical operation system given above.

As illustrated in FIG. 21, the surgical operation system 400 includes: an elongate cutting edge 401; a hand piece 402 serving as a seizure member connected to the cutting edge 401; a control unit 403 to which the hand piece 402 is connected; a foot switch 404 connected to the control unit 403; and an unillustrated sheath for introducing the cutting edge into an articulatory cavity. Prepared is a washing brush 408 for washing the cutting edge 401.

The system 400 in this embodiment prepares three types of cutting edges 401 such as a straight type cutting edge 401A having $\phi 5$, a bend type cutting edge 401B of $\phi 5$ and a straight type cutting edge 401C of $\phi 3$.

The cutting edge 401 is constructed as follows. An internal tube is rotatably inserted into an external tube 411. The edge(s) is formed at the tip(s) of only the internal tube or both the external tube 411 and the internal one. An external tube connecting member 414 having a large diameter is formed at the rear end of the external tube 411. The rear end of the internal tube is protruded backwards from the connecting member 414. An internal tube connecting member 415 is formed at the rear end of the connecting member 414. A hollow portion of the internal tube is employed as a suction passageway. The side portion of the internal connecting member 415 is formed with a suction port 416 communicating with the suction passageway.

Prepared as the hand piece 402 are two types of hand pieces 402A and 402B connectable to all of three types of cutting edges 401. The hand piece 402 includes its body 412 which incorporates a motor 422 (not shown in FIG. 21) for rotationally driving the internal tube of the cutting edge 401. The top end of the body 421 is provided with a connecting member 423 connectable to the inner tube connecting member 415 as well as to the external tube connecting member 414. An output shaft of the motor 422 is linked to the internal tube connecting member 415. The rear end of the body 421 is formed with a suction hose connecting member 424 communicating with the suction port 416 of the cutting edge 401. Connected to the rear end of the body 421 is a cord 425 for transmitting/receiving the electric power of for the motor 422 and signals which will be mentioned later. The terminal of the cord 425 is provided with a connector 426 detachably connected to the control unit 403.

Two types of washing brushes 408 are prepared for a large diameter and a small diameter.

Figure 22:
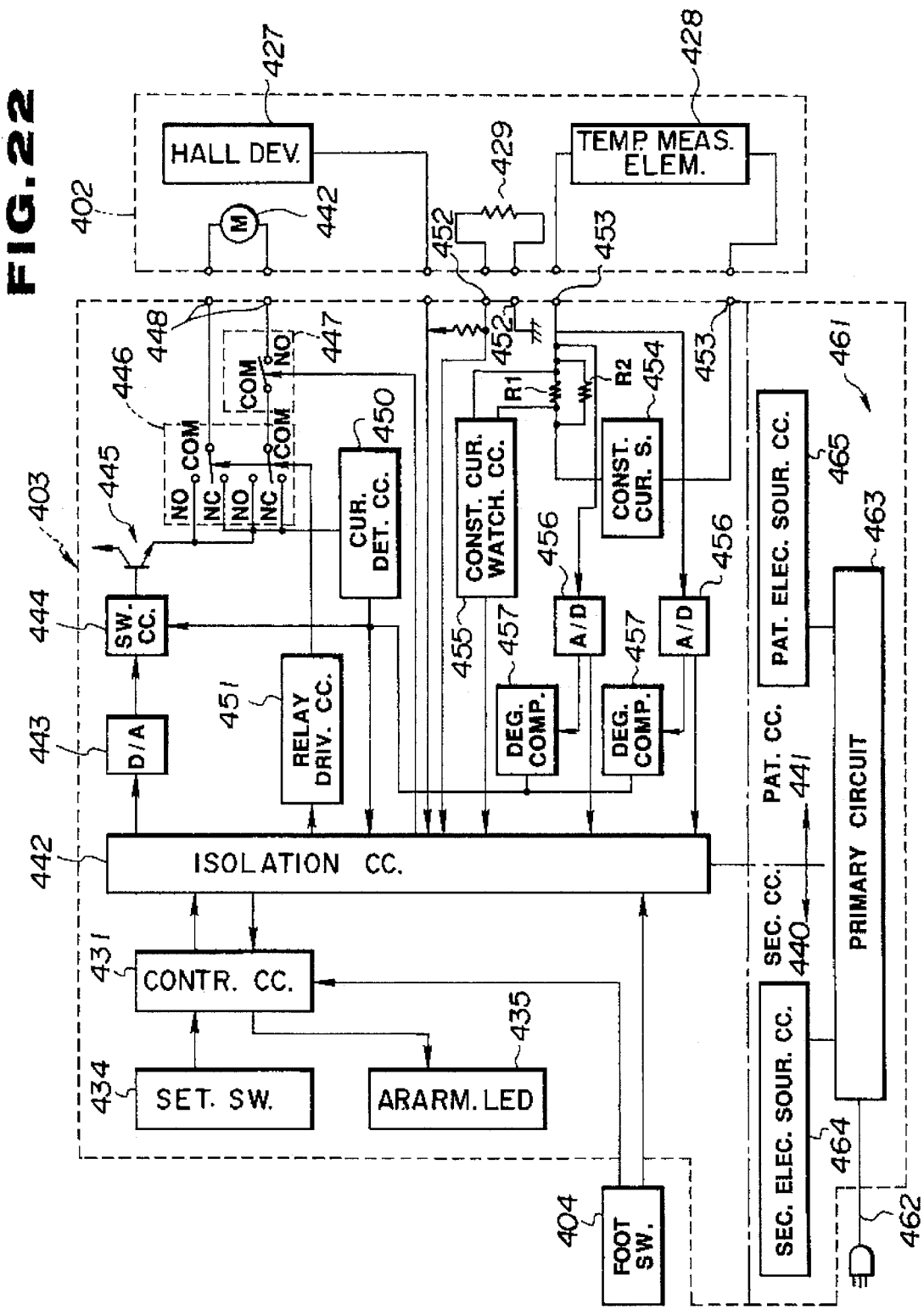

The following is a description of the hand piece 402 and circuitry of the control unit 403 with reference to FIG. 22.

The hand piece 402 comprises: a motor 422 for rationally driving the internal tube of the cutting edge 401; a Hall element 427 for detecting the number of revolutions of the motor 422 in cooperation with an unillustrated magnet; a temperature measuring element 428, composed of a platinum temperature sensor or the like, for detecting a temperature of the hand piece 402; and a resistance 429 for discriminating the type of the hand piece mounted on the connector 426. These components are connected via the connector 426 to the control unit 403.

On the other hand, the control unit 403 includes a control circuit 431. Connected to this control circuit 431 are a set switching 434, an alarm LED 435 and also a foot switch 404. The foot switch 404 is of a tandem type. When treading, e.g., a right pedal, the motor 422 rotates forwards (rightward rotations). Whereas a left pedal is treaded, the motor 422 rotates reversely (leftward rotations). If the two pedals are treaded, the motor makes the forward and reverse rotations. The set switch 434 is capable of setting the number of revolutions of the motor 422. The control circuit 431 outputs a revolution number digital signal set by the set switch in response to a signal for indicating treading of the foot switch 404. This digital signal is isolated by an isolation circuit 442 composed of, e.g., a photocoupler for isolating a patient circuit 440 from a secondary circuit 441. The digital signal is converted into an analog signal by means of a D/A converter 443. A voltage value of the analog signal corresponds to the number of revolutions of the motor 422. The analog signal is, after passing through a switch circuit 444, applied to a base of a transistor 445. An electric source voltage is impressed on a collector of the transistor 445. An emitter thereof is connected to respective fixed contact points NO, NO of a bipolar relay 446. A current detecting circuit 450 is connected to respective fixed contact points NC, NC of the relay 446. One movable contact point COM of the relay 446 is connected directly to contact points 448, 448 of a hand piece connector receiver to which the hand piece 402 is connected. Another movable contact point COM is connected via a relay 447 to the same contact points. The motor 422 of the hand niece 402 is connected to those contact points 448, 448. The relay 447 is driven by a relay driving circuit 451. The relay driving circuit 451 is connected via the isolation circuit 442 to the control circuit 431, whereby the circuit 451 is controlled by the control circuit 431. Outputs of the current detecting circuit 450 are inputted to the switch circuit 444 and further to the control circuit 441 through the isolation circuit 442.

The relay 447 is opened and closed in response to signals of the switch 404 through the isolation circuit 442.

Signals of the Hall element 427 within the hand piece 402 are inputted to the control circuit 431 via the connector 426, the hand piece connector receiver and the isolation circuit 442.

The hand piece connector receiver is equipped with terminals 452, 452 connected to a discrimination resistance 429 of the hand piece 402. The electric source voltage is applied to one terminal 452, while another terminal 452 is earthed. One terminal 452 is connected via the isolation circuit 442 to the control circuit 431. The control circuit 431 discerns the type of the hand piece 402 on the basis of an inter-terminal voltage of the resistance 429.

The hand piece connector receiver has terminals 453, 453 connected to the temperature measuring element 428 within the hand piece 402. Connected to the terminals 453, 453 is a constant current source 454 for feeding a constant current to the temperature measuring element 428. Two pieces of parallel resistances R1 and R2 are connected in series to the constant current source 454. Note that resistance values of the resistances R1 and R2 are equalized.

Connected to both ends of the resistances R1 and R2 is a constant current watch circuit 455 for watching whether the current flowing in the temperature measuring element 428 is an appropriate constant current or not. An output of the constant current watch circuit 455 is inputted via the isolation circuit 442 to the control circuit 431. Connected to one terminal 453 are two A/D converters 456, 456 for converting voltages generated at both ends of the temperature measuring element 428 into digital signals. Output signals of the A/D converters 456, 456 are inputted via the isolation circuit 442 to the control circuit 431. The output signals of the A/D converter 456, 456 are inputted to digital comparators 457, 457, wherein the signals are compared with a predetermined threshold level. Outputs of the digital comparators 457, 457 are inputted to the switch circuit 444.

The electric power is supplied from an electric source unit 461 to the respective constituent circuits incorporated in the control unit 403.

The electric source unit 461 consists of: a primary circuit 463 in which an AC cord 462 fitted with an AC plug is connected to a primary winding; a secondary electric source circuit 464 supplied with the electric power in an isolated state from the commercial electric source by the primary circuit 463; and a patient electric source circuit 465. The secondary electric source circuit 464 supplies the driving electric power to the control circuit 431 constituting the secondary circuit 440. The patient electric source circuit 465 feeds the driving electric power to the respective circuits combined to constitute the patient circuit 441.

This embodiment, as in the first embodiment, adopts a means for reducing the emission/permeation of noises.

Next, the operation (different from that of the electronic endoscope) of this embodiment will be described.

Any one of the hand pieces 402A and 402B is selected according to the application, and the selected one is connected to the control unit 403. One of the cutting edges 401A, 401B and 401C is selected according to the application, and the selected one is connected to the hand piece 402. When driving the motor 422 within the hand piece 402, the internal tube of the cutting edge 401 is rotationally driven. An excising treatment is effected by means of the edge formed at the tip thereof. A piece of excised tissue is sucked via the suction passageway formed inside the internal tube by the suction unit connected via the hose to the suction hose connecting unit 424, thus removing the excised tissue.

The control circuit 431 of the control unit 403 discriminates the type of the connected hand piece 402 with the aid of the discrimination resistance 429 provided at the connector 426 of the hand piece 402. Two types of hand pieces 402A and 402B are drivable based on different characteristics.

The foot switch 404 is used for controlling the rotating direction of the motor 422 and ON/OFF of the rotations thereof. The signals of the foot switch 404 are transmitted to the relay 446 via the control circuit 431, the isolation circuit 442 and the relay driving circuit 451. The signals of the foot switch 404 are also transmitted via the isolation circuit 442 to the relay 447.

The control circuit 431 outputs a digital signal representing the set number of revolutions in response to the signal indicating the fact that the foot switch 404 is treaded. The digital signal isolated by the isolation circuit 442 is converted into an analog signal by the D/A converter 443. This analog signal is fed via the switch circuit 444 to the motor 422.

A current flowing into the motor 422 is detected by the current detecting circuit 450. If the current overflows in excess of a current value set by this detecting circuit 450, the switch circuit 444 is opened, thereby stopping the supply of electric power to the motor 342.

The signals, taken in the control circuit 431, of the foot switch 404 are transmitted via the isolation circuit 402 to the relay driving circuit 451. The relay driving circuit 451 switches the relay 446 in accordance with setting (forward and reverse rotations) of the foot switch 404.

On the other hand, the signals of the foot switch 404 serve to directly switch the relay 447 through the isolation circuit 442. Namely, the motor 442 is directly turned ON/OFF.

In this manner, the signals of the foot switch 404 are classified into two types—i.e., one signal (corresponding to software) passing through the control circuit 431 and the other (corresponding to hardware) being transmitted directly to the relay 447 to switch ON/OFF the motor 422. The motor 422 can not be turned ON unless these two types of signals are prepared.

If the current detecting circuit 450 is brought into a fault, there may exist a possibility that the motor 422 can not be stopped even when the current overflows into the motor 422. To cope with this situation, according to this embodiment, the normal operation can be held even if one system goes wrong by virtue of the current detecting circuit 450 (the circuitry of which is not illustrated). In this embodiment, as discussed above, there is taken a countermeasure against the single fault case (SFC) with respect to the output control system.

Overheating of the hand piece 402 is prevented in the following manner.

A current (I) is fed from the constant current source 454 to the temperature measuring element 428. At this time, voltages of R.I are generated at both ends of the temperature measuring element 428 because of a resistance (R) of the temperature measuring element 428. A resistance value of the element 428 varies with changes in temperature (in this embodiment, the resistance increases with a higher temperature). Hence, the voltages produced at both ends of the element 428 contain information on the temperatures. The thus generate voltages are converted into digital signals by the A/D converters 456, 456. The digital signals are inputted as temperature information to the control circuit 431. When detecting a predetermined first temperature from the temperature information, the control circuit 431 flashes or lights up the alarm LED 435 on the front panel. The control circuit 431, when detecting a predetermined second temperature higher than the first temperature, stops the supply of electric power to the motor 422 through the D/A converter 443.

A threshold level of the digital comparators 457, 457 is set to a digital value corresponding to the second temperature. If the output of the A/D converters 456, 456 exceeds the value corresponding to the second temperature, the switch circuit 444 is opened by the outputs of the digital comparators 457, 457. The supply of electric power to the motor 422 is thereby stopped not via the control circuit 431 but directly. In this manner, the motor stop control can be performed in the two systems, i.e., via the control circuit 431 and via the digital comparator 457. As a result, more safety can be secured. The constant current source 454 is watched by the constant current watch circuit 455. If this is not an appropriate constant current, the motor 422 is stopped via the control circuit 431. In this embodiment also, the isolation circuit 442 serves to isolate the secondary circuit 440 from the patient circuit 441. These circuits 440 and 441 are at the same time isolated from the commercial electric source. Therefore, in the event of an accident, the safety can be secured.

Because of providing the means for reducing the emission/permeation of noises, the malfunction can be prevented. The system exhibiting the high safety can be actualized. An additional merit is to exert no adverse influence on other units.

Figure 23:
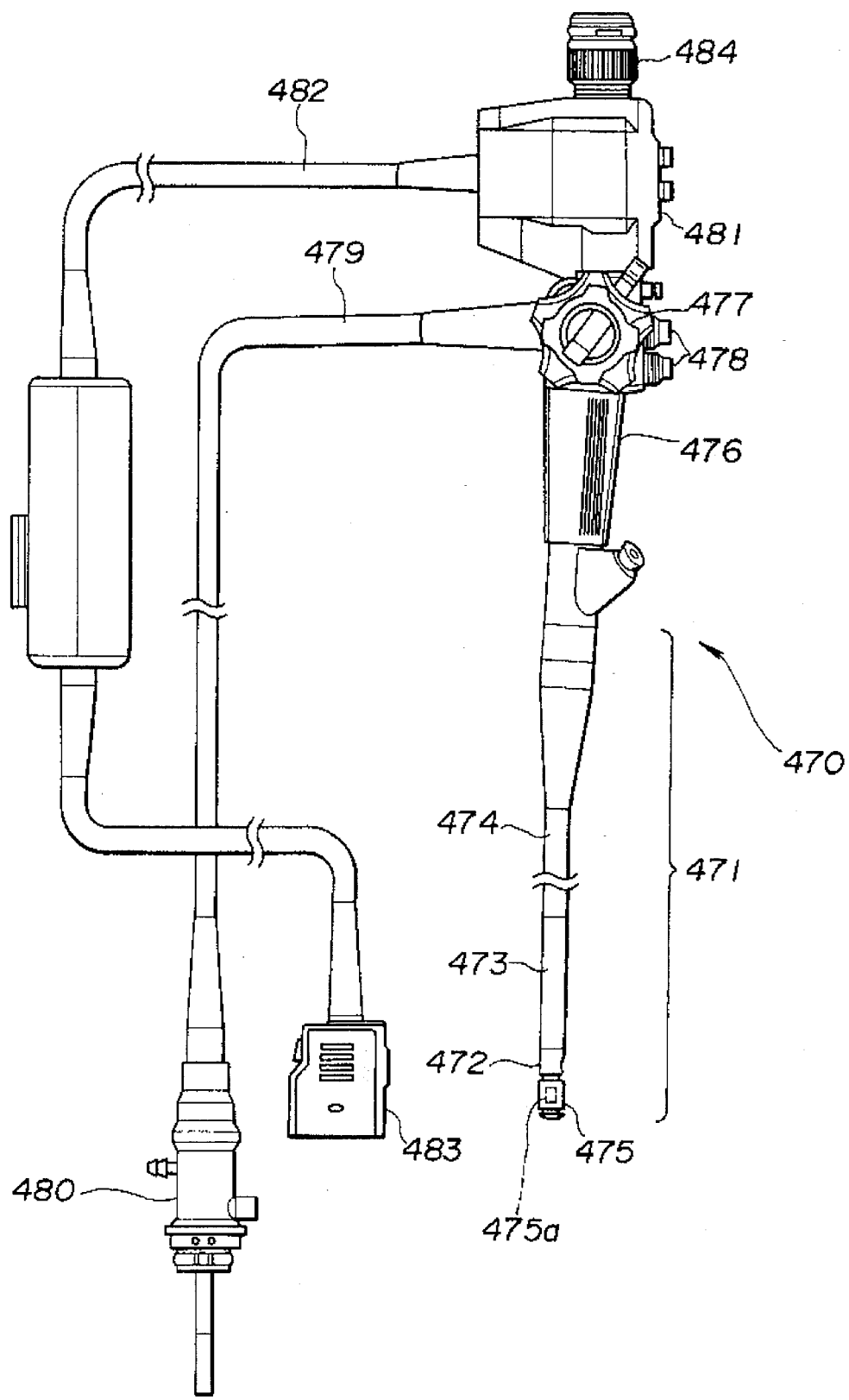
FIGS. 23 and 24 in combination show a fifth embodiment of this invention.

FIG. 23 illustrates an ultrasonic endoscope 470 in a fifth embodiment of this invention.

The ultrasonic endoscope 470 includes an intubation unit 471. The intubation unit 471 is composed of a tip member 472, a bend member 473 and a flexible member 474. The tip member 472 is formed with an ultrasonic probe 475 having a built-in ultrasonic vibrator 475a for transmitting/receiving ultrasonic waves. An endoscope manipulation unit 476 is connected to the rear end of the intubation unit 471. The endoscope manipulation unit 476 is equipped with a bend manipulating knob 477 for curvilinearly manipulating the bend member 473 and with an air blow/water supply button 478. A universal cord 479 is connected to the endoscope manipulation unit 476. The top of the universal cord 479 is provided with a connector 480 connected to an unillustrated light source.

Provided at the rear end of the endoscope manipulation unit 476 is an auxiliary manipulation unit 481 for drive-manipulating the ultrasonic probe. An electric cable cord 482 is connected to the auxiliary manipulation unit 481. The top end of the electric cable cord 482 is provided with a connector 483 connected to an ultrasonic observation apparatus 469 shown in FIG. 24. Note that the numeral 484 represents an ocular unit disposed at the rear end of the auxiliary manipulation unit 481. The ocular unit 484 is positioned upwardly of a gravity of the endoscope manipulation unit 476.

The auxiliary manipulation unit 481 accommodates a motor for rotationally driving the ultrasonic vibrator 475a.

Figure 24:
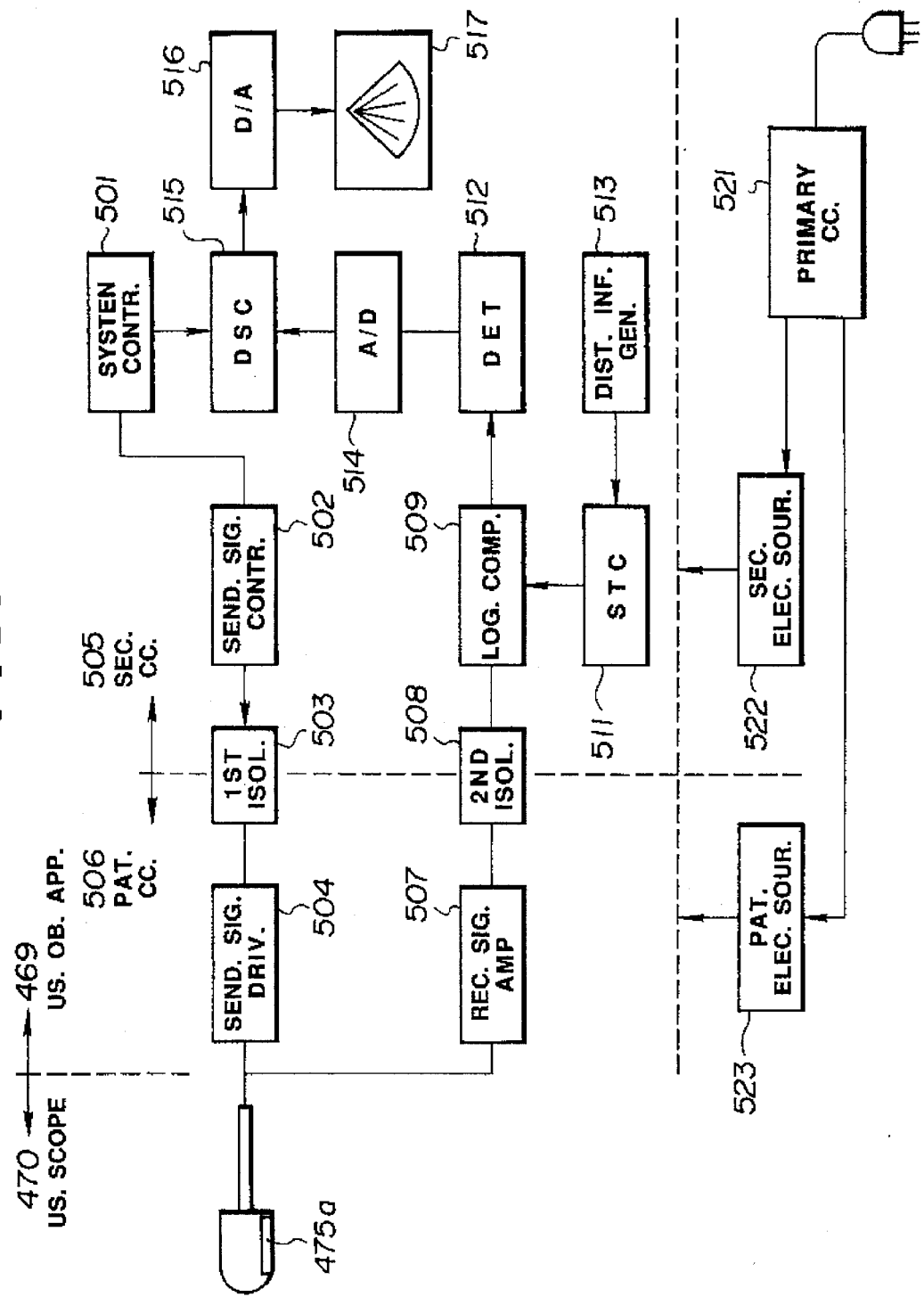

FIG. 24 depicts a construction of a signal processing system of the ultrasonic endoscope system in the fifth embodiment.

Under control of a system controller 501, a transmitting signal control circuit 502 drives a transmission driving circuit 504 through a first isolation circuit 503, thereby outputting transmitting pulses.

The isolation circuit 503 isolates a secondary circuit 505 from a patient circuit 506.

The transmitting pulses are applied to the ultrasonic vibrator 475a. The ultrasonic waves are thereby transmitted from the vibrator 475a. The ultrasonic waves transmitted are reflected by discontinuous portions of an acoustic impedance. The reflected ultrasonic waves are received again by the ultrasonic vibrator 475a, whereby the waves are converted into electric signals. The (received) signals are inputted to a receiving signal amplifier circuit, wherein the signals are amplified. Thereafter, the signals are inputted via a second isolation circuit 508 to a logarithm compression circuit 509. The logarithm compression circuit 509 adds gain control signals based on an ATC circuit 511 and logarithm-compresses the input signals. The thus compressed signals are then outputted to a detection circuit 512.

Depth (distance) information which is to be gain-adjusted is inputted from a distance information generation circuit 513 to the STC circuit 511. Gain signals corresponding to the information are outputted to the logarithm compression circuit 509. Characteristics of the logarithm compression are variable corresponding to the distances.

The receiving signals detected by the detection circuit 512 are converted into digital signals by means of an A/D converter 514. The digital signals are inputted to a digital scan converter (abbreviated to DSC) 515. The DSC 515 stores the inputted digital signals into a frame memory. The data stored therein are read in synchronization with standard TV signals. The data are converted into analog signals by a D/A converter 516, thereby displaying an ultrasonic tomography image on a monitor 517.

In this embodiment also, the isolation from the commercial electric source is attained by the primary circuit 521. The electric power of a predetermined voltage is supplied to a secondary electric source circuit 522 and a patient electric source circuit 523.

The respective electric source circuits 522 and 523 effect conversions into predetermined DC voltages. The circuits 522 and 523 supply the driving electric power to the individual circuits which constitute the secondary circuit 505 and the patient circuit 506.

As in the first embodiment, the means (not shown) for reducing the noises is provided similarly in this embodiment. Hence, this embodiment exhibits the same action and effects as those of the first embodiment.

Figure 25:
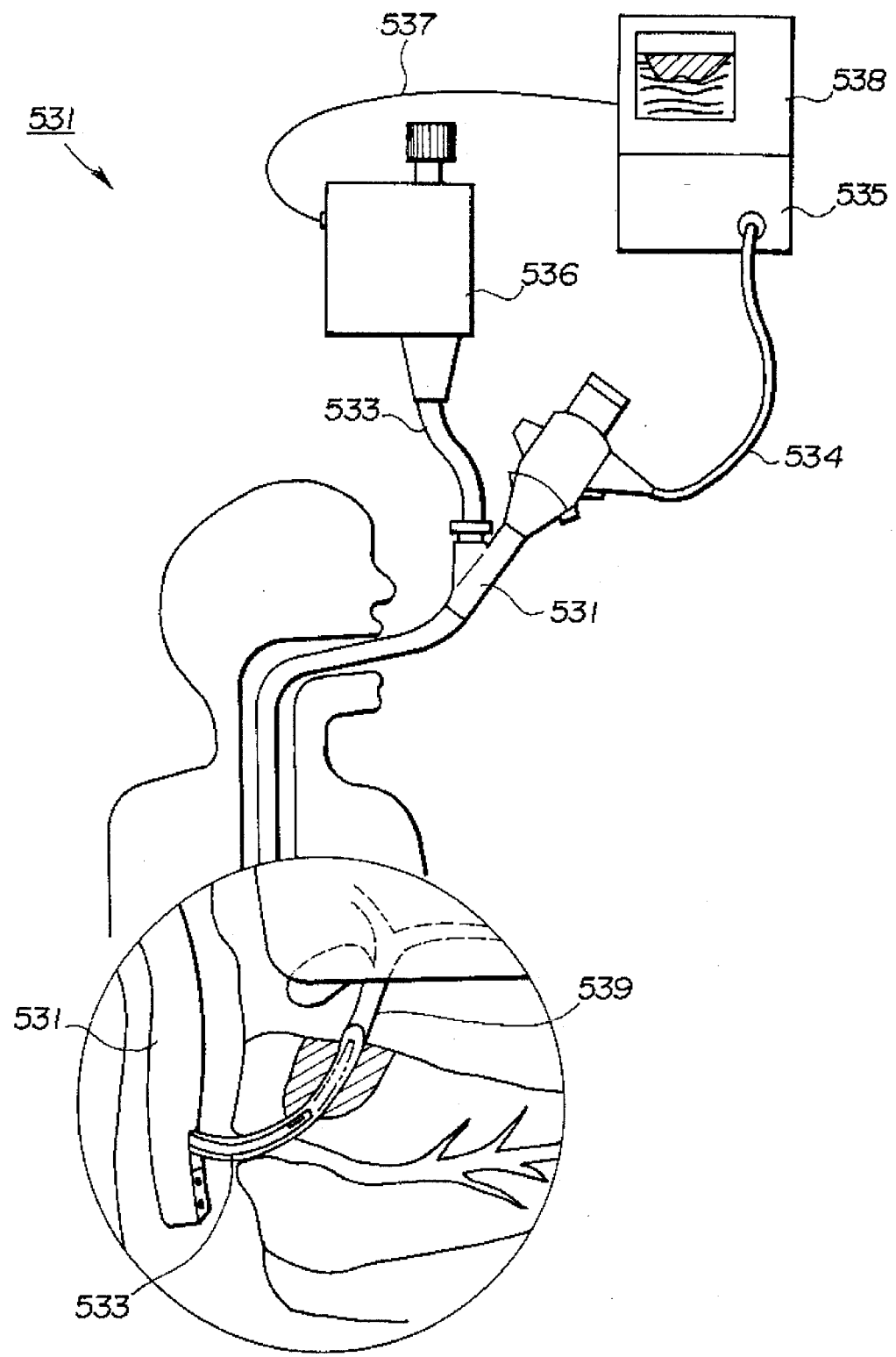
FIG. 25 shows a variant form of the fifth embodiment.

FIG. 25 shows an ultrasonic endoscope system 531 as a variant form of the fifth embodiment.

The endoscope system 531 is constructed such that an ultrasonic probe 533 is inserted in a channel formed in an endoscope 532. In the endoscope 531, a light guide cable 534 is connected to a light source 535, whereby the illumination light is supplied.

A manipulation unit 536 of the ultrasonic probe 533 accommodates a motor for rotating the ultrasonic vibrator. An electric cable 537 extending from the manipulation unit 536 is connected to an ultrasonic observation apparatus 538.

The ultrasonic vibrator accommodates a transmission driving circuit for sending a transmitting signal and a receiving signal amplifier circuit.

A configuration of the signal processing system in this variant form is the same as that of the fifth embodiment.

FIG. 25 shows a situation where the ultrasonic probe 533 passes through the channel, and its tip is introduced into a bile duct 539.

Figure 26:
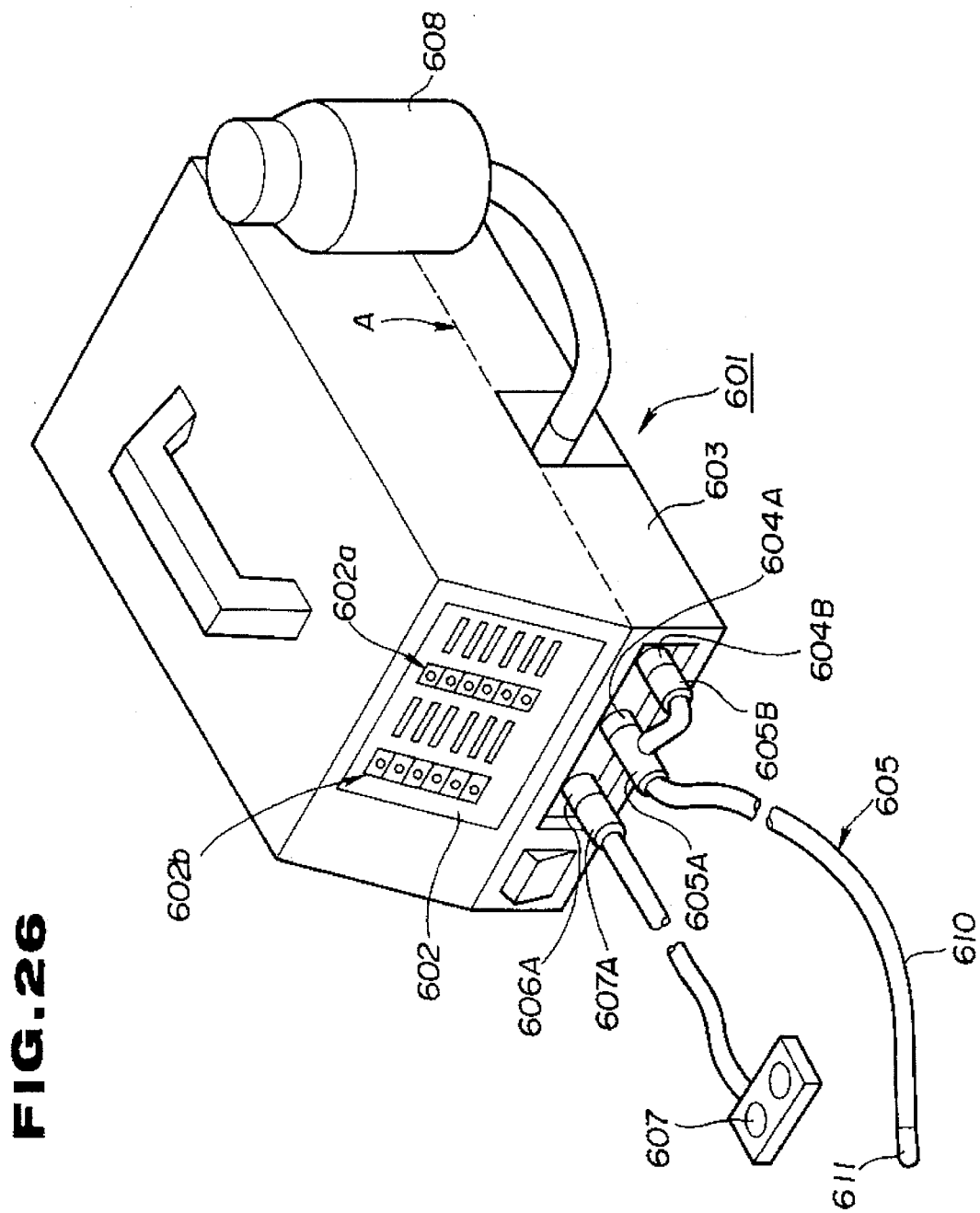
FIGS. 26 and 27 in combination show a sixth embodiment of this invention.

Turning to FIG. 26, there is illustrated a burning anastaltic device 601 in a sixth embodiment of this invention.

Figure 27:
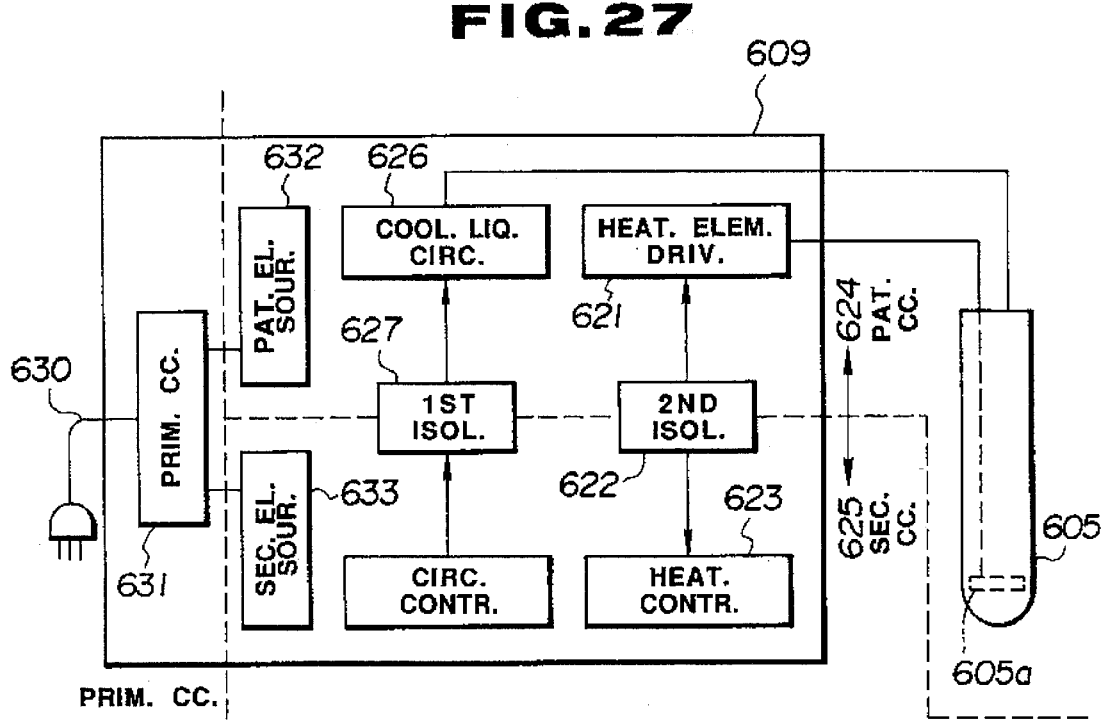

As depicted in FIG. 26, the burning anastaltic device 601 in the sixth embodiment comprises, an electric source box 603, an elongate heat probe 605, a foot switch unit 607, a water supply tank 608 and a probe driving circuit 609. The electric source box 603 includes a manipulation panel 602 mounted on a front oblique surface. The heat probe 605 includes connectors 605A and 605B which are detachably attached to connector receivers 604A and 604B disposed at the lower part of the front surface of the electric source box 603. The foot switch unit 607 includes a connector 607A detachably attached to a connector receiver 606A provided at the lower part of the front surface of the box 603. The tank 608 is mounted on the side surface thereof. The probe driving circuit 609 shown in FIG. 27 is encased in the box 603.

The heat probe 605 is conductive to an exothermic element (heat element) accommodated in a tip member 611 through a flexible probe unit 610 having a small diameter and insertable into a hollow channel of the unillustrated endoscope. For this purpose, a coaxial cable is inserted through the probe unit 610 which is in turned formed with a water supply passageway for supplying the washing water. The electric connector 605A and the water supply connector 605B, which are disposed on this side of the heat probe 605, are fitted to the connector receivers 604A and 604B of the electric source box 603. The connector 607A of the foot switch unit 607 is attached to the connector receiver 606A of the box 603. In this state, the washing liquid is fed from the water supply tank 608 via the water supply passageway by depressing a water supply (washing) switch of the foot switch unit 607. The liquid is injected from a nozzle of the tip member 611 of the heat probe 605 towards the affected part, thus washing this part. When depressing a heating switch of the foot switch unit 607, the heat element is heated up through the coaxial cable. The part, which is pressed by the tip member 611, is thus subjected to a cure treatment such as an anastaltic treatment.

Note that an injection quantity of the washing liquid and a heating quantity of the heat element are selectively settable depending on the effected parts by use of set buttons 602a and 602b provided on the panel 602.

In order to handle the electric system and the water supply system, the electric source box 603 houses an intermediate chassis in a position indicated by, e.g., a broken line A in the box 603 depicted in FIG. 26 to separate the upper electric system from the lower water supply system. A water supply pump is accommodated in a water-proof frame, thus securing the safety. After working separately in the respective systems, a complete product is attainable by assembling. The manufacturing steps are thus simplified.

Next, the signal processing system will be explained with reference to FIG. 27.

The heat element 605a accommodated in the tip member of the heat probe 605 is supplied with a heating current from a heat element driving circuit 621. Detected are voltages at both ends of an unillustrated resistance within the driving circuit 621. A temperature of the heat element 605a is detected by a heat control circuit 623 through a first isolation circuit 622. The control circuit 623 controls the heating current to keep a predetermined temperature of the element 605a. The first isolation circuit 622 isolates a patient circuit 624 from a secondary circuit 625. The heat probe 605 is controlled by a cooling liquid circulation circuit 626 so that a cooling liquid is circulated. This cooling liquid circulation circuit 626 is controlled by a circulation control circuit 628 through a second isolation circuit 627.

The respective circuits combined to constitute the patient circuit 624 and the secondary circuit 625 are insulated from the commercial electric source by a primary circuit 631 connected to an AC cord 630. Those circuits are supplied with predetermined driving voltages from a patient electric source circuit 632 and a secondary electric source circuit 633.

In this embodiment also, the means (not shown) for reducing the noises are, as in the first embodiment, provided in the individual units. In accordance with this embodiment, the burning anastaltic treatment can completely be performed without undergoing any influence by the noises. The noises which are to be released outside can be reduced. As a result, no adverse influence is exerted on the external units.

Figure 28:
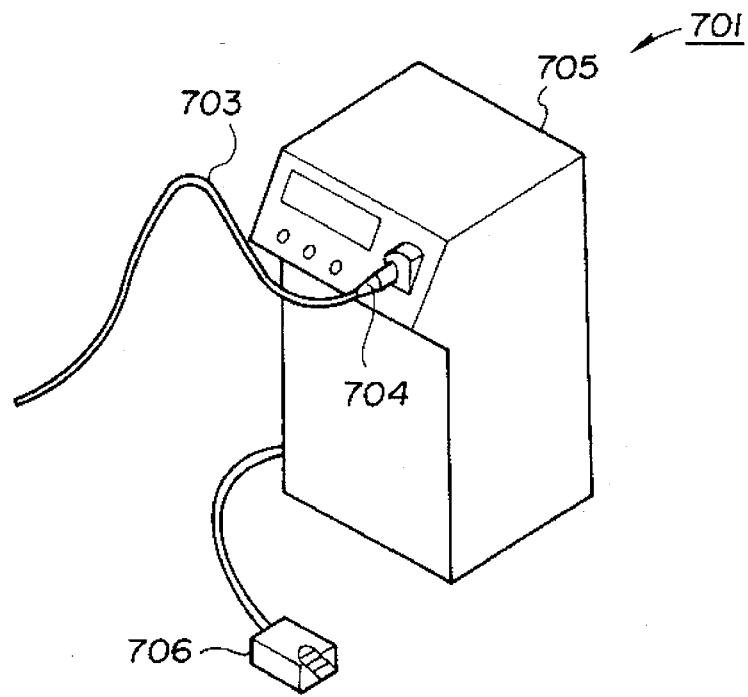
FIGS. 28 to 30 in combination show a seventh embodiment of this invention.

FIG. 28 shows an electrohydraulic lithotriptor (abbreviated to EHL) 701 in a seventh embodiment of this invention.

The EHL 701 functions to crush an intravital calculus by impulsive waves caused by discharging. The EHL 701 is one of effective means for crushing the intravital calculus in combination with the endoscope through an observation by this endoscope.

The EHL 701 comprises: an elongate discharge probe 702 having an electrode (see FIG. 29) for effecting discharging; a discharge control unit 705 for supplying discharge electric power to the discharge probe 703 by mounting a connector 704 on its proximal end of the probe 703; and a discharge operating watt switch 706.

Figure 29A:
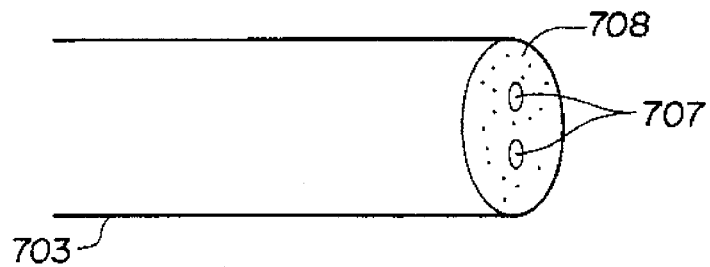
Figure 29B:
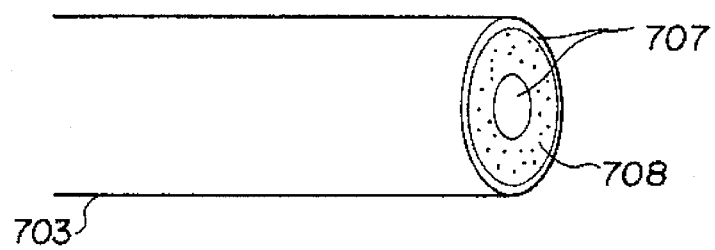

FIGS. 29a and 29b depict configurations of the tip of the discharge probe 703.

Referring to FIG. 29a, for keeping constant a distance between two lengths of electrodes 707, 707, the peripheries thereof are molded with a cylindrical insulating material 708. The electrodes 707, 707 are exposed from the tip end surface. A gap therebetween is set enough to effect discharging by a voltage supplied from the discharge control unit 705.

Referring to FIG. 29b, the two lengths of electrodes 707, 707 are set coaxial. The insulating material 708 is interposed therebetween.

Figure 30:
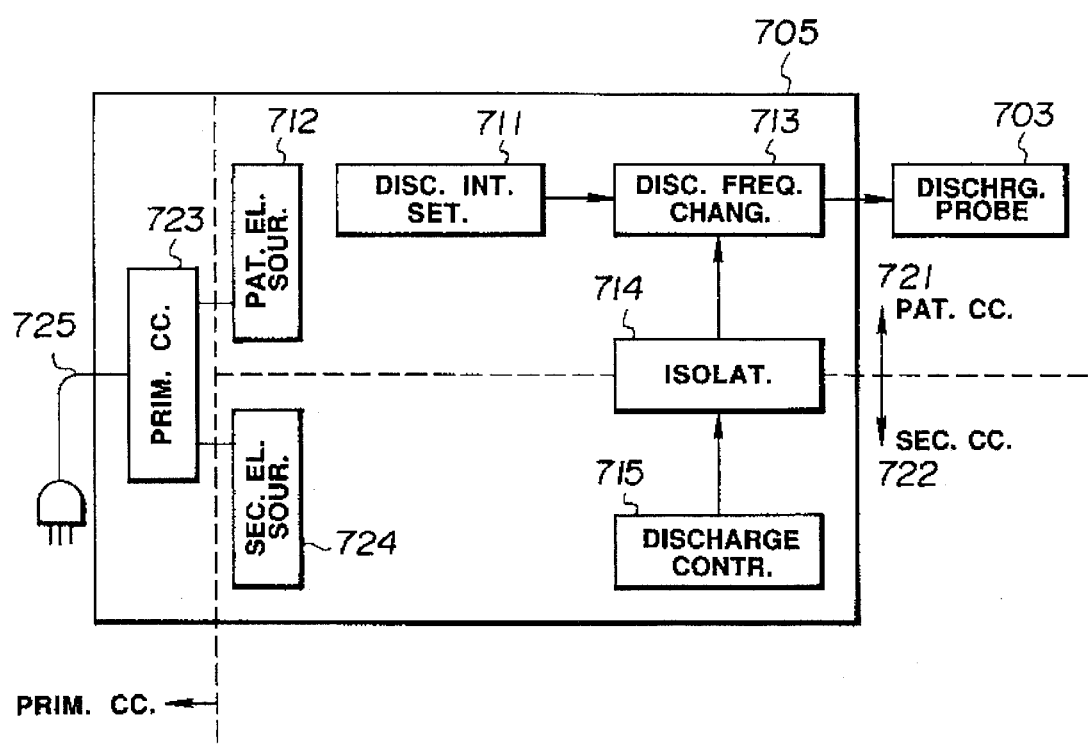

FIG. 30 shows a construction of the signal system of the EHL 701.

A discharge intensity set circuit 711 consists of a plurality of capacitors and a plurality of switches for switching ON/OFF the respective capacitors. The number of switch-ON capacitors is selected, whereby an intensity of a discharge energy can be set. The circuit 711 is supplied with a DC voltage employed for discharging from a patient electric source circuit 712.

An output of the discharge intensity set circuit 711 works to supply the electric power to cause discharging of the discharge probe 703 via a discharge frequency changeover circuit 713. The changeover circuit 713 is composed of an ON/OFF switch. The ON/OFF states of the switch can be variably set enough to perform discharging several times by use of the discharge control circuit 715 through an isolation circuit 714, if the calculus can not be crushed by a single step of discharging.

The discharge control circuit 715 is constructed of: a timer for setting a time-interval (frequency) for specifying the number of discharging operations effected per unit time; and a counter for setting the specific number of discharging operations on the whole.

The isolation circuit 714 is intended to isolate a patient circuit 721 from a secondary circuit 722. This embodiment also involves the use of a primary circuit 723 to which an Ac cord 725 is connected and a secondary electric source circuit 724.

In this embodiment, there are similarly provided the means (not shown) for reducing the noises.

Note that different embodiments can be configured by combining the embodiments discussed above. Those embodiments also come under the present invention.

Although the illustrative embodiments of the present invention have been described in detail with reference to the accompanying drawings, it is to be understood that the present invention is not limited to those embodiments. Various changes or modifications may be effected therein by one skilled in the art without departing from the scope or spirit of the invention.

What is claimed is:

1. An electronic endoscope system comprising:

an electronic endoscope including: an intubation unit intubatable into a body cavity; an image forming optical system, provided at a tip of said intubation unit, for forming an optical image; a solid-state imaging element for photoelectrically converting the optical image based on said image forming optical system; an illumination light from the tip of said intubation unit; and a first connector portion, having one end connected to said solid-state imaging element, through which a plurality of signal lines are inserted;

a patient circuit drive signal generating means for applying a drive signal to said solid-state imaging element through a second connector portion to which said first connector portion is detachably connected; and an amplifier circuit for amplifying at least an image signal outputted from said solid-state imaging element upon applying the drive signal;

a secondary circuit including a video signal processing circuit, having its ground conductive to the earth, for generating a standard video signal from the image signal transmitted via said amplifier circuit;

an isolation means for isolating said patient circuit from said secondary circuit;

a monitor means for displaying the standard video signal; and a noise reducing means, provided in at least one of said electronic endoscope, said patient circuit and said secondary circuit for reducing radiation/permeation of noises, wherein at least one of said first connector portion and said second connector portion includes at least one shield gasket member formed of flexible and deformable conductive material and molded in a spring-like configuration for decreasing a contact resistance to a metal frame body of said second connector portion.

2. An electronic endoscope system as recited in claim 1, further comprising a cable branched off, on the way to said first connector portion, to a second connector portion, wherein said second connector portion includes said shield gasket member for decreasing the contact resistance to a metal frame body of said second connector portion.

3. The electronic endoscope system as recited in claim 2, wherein said first connector portion includes a shield gasket member formed of flexible and deformable conductive material and molded in a spring-like configuration for decreasing the contact resistance to a metal frame body of said first connector portion.

4. An electronic endoscope system as recited in claim 1, further comprising a third connector portion detachably connecting said first connector portion and said second connector portion, wherein said shield gasket member is included between said first connector portion and said third connector portion.

5. An electronic endoscope system as recited in claim 1, further comprising a third connector portion detachably connecting said first connector portion and said second connector portion, wherein said shield gasket member is included between said second connector portion and said third connector portion.

* * * * *